United States Patent [19]

Buechler et al.

[11] Patent Number: 5,028,535

[45] Date of Patent: Jul. 2, 1991

[54] THRESHOLD LIGAND-RECEPTOR ASSAY

[75] Inventors: Kenneth F. Buechler, Santee; Gunars E. Valkirs, Escondido; Richard R. Anderson, Encinitas, all of Calif.

[73] Assignee: Biosite Diagnostics, Inc., San Diego, Calif.

[21] Appl. No.: 295,568

[22] Filed: Jan. 10, 1989

[51] Int. Cl.$^5$ .............................................. G01N 33/53
[52] U.S. Cl. .................................. 435/7.1; 435/7.500; 435/7.900; 435/7.920; 435/7.930; 435/7.940; 435/805; 435/810; 435/967; 436/501; 436/514; 436/518; 436/523; 436/524; 436/525; 436/526; 436/527; 436/528; 436/529; 436/530; 436/531; 436/807; 436/810; 436/825
[58] Field of Search ..................... 435/7, 805, 810, 7.1, 435/7.5, 7.9, 7.92, 7.93, 7.94, 967; 422/55–57; 436/501, 514, 518, 523–531, 807, 810, 825

[56] References Cited

U.S. PATENT DOCUMENTS

| | | | |
|---|---|---|---|
| 3,654,090 | 4/1972 | Shuurs et al. ..................... | 195/103.5 |
| 3,878,187 | 4/1975 | Schneider et al. .................. | 530/363 |
| 3,884,898 | 5/1975 | Schneider ........................... | 530/363 |
| 4,120,945 | 10/1978 | Gutcho et al. ..................... | 436/53 X |
| 4,125,372 | 11/1978 | Kawai et al. ......................... | 23/230 |
| 4,168,146 | 9/1979 | Grubb et al. ......................... | 23/230 |

(List continued on next page.)

FOREIGN PATENT DOCUMENTS

| | | |
|---|---|---|
| 0032286 | 7/1981 | European Pat. Off. . |
| 0203238 | 3/1986 | European Pat. Off. . |
| 0200381 | 11/1986 | European Pat. Off. . |
| 0253464 | 1/1988 | European Pat. Off. . |
| 0267006 | 5/1988 | European Pat. Off. . |
| 0271204 | 6/1988 | European Pat. Off. . |
| 8606170 | 10/1986 | World Int. Prop. O. . |

OTHER PUBLICATIONS

Lee, S. & Liberti, P. A., *Analytical Biochem.*, 166:41–48 (1987).
Ekins, R. P., et al., "Theoretical Aspects of Saturation and Radio Immunoassay" in Radioisotopes in Medicine: In Vitro Studies, (Goswitz & Murphy eds.), U.S. Atomic Energy Comm'n, Oak Ridge, TN, 9–100 (1968).
Rodgers, R., et al., *Clin. Chem.* 24:95–100 (1978).
Liu, D. et al., *Clin. Toxicology*, 25:527–538 (1987).
Pluskal, M. G. et al., *BioTechniques*, 4:272–283 (1986).
Zettner, A., *Clin. Chem.* 19:699–705 (1973).
Yalow, R. S. & Berson, S. A., "General Principles of Radio Immunoassay" in Radioisotopes in Medicine: In Vitro Studies (Goswitz & Murphy eds.), U. S. Atomic Energy Comm'n, Oak Ridge, TN 7–41 (1968).
T. Chard, Laboratory Techniques in Biochemistry and Molecular Biology: An Introduction to Radio-Immunoassay and Related Techniques, (Elsevier Biomedical Press 1982), pp. 1–26 and 169–184.

*Primary Examiner*—Robert J. Warden
*Assistant Examiner*—Carol A. Spiegel
*Attorney, Agent, or Firm*—Mary S. Consalvi

[57] ABSTRACT

This invention is directed to a ligand-receptor assay for determining the presence or amount of at least one target ligand, capable of competing with a ligand analogue conjugate for binding sites available on a ligand receptor, said ligand analogue conjugate comprising at least one ligand analogue coupled to a signal development element capable of emitting a detectable signal, in a fluid sample suspected of containing said target ligand, comprising the steps of:

a. contacting said fluid sample with ligand analogue conjugate and ligand receptor to form a reaction mixture, the relative amounts of ligand analogue conjugate and ligand receptor being such that in the absence of target ligand, and subsequent to substantially equilibrium binding, substantially all of the ligand analogue conjugate is bound to ligand receptor;

b. detecting the unbound ligand analogue conjugate;

c. relating the detectable signal to the presence or amount of target ligand in the fluid sample. In one embodiment an optional means also is employed for removing receptor from the reaction mixture. In related claimed assay formats the analyte of interest may be either ligand receptor or ligand.

70 Claims, 3 Drawing Sheets

U.S. PATENT DOCUMENTS

| | | | |
|---|---|---|---|
| 4,200,690 | 4/1980 | Root et al. | 435/7 |
| 4,203,802 | 5/1980 | Rubenstein et al. | 435/7 |
| 4,233,402 | 11/1980 | Maggio et al. | 435/7 |
| 4,246,339 | 1/1981 | Cole et al. | 435/7 |
| 4,277,437 | 7/1981 | Maggio | 435/7 X |
| 4,281,065 | 7/1981 | Lin et al. | 435/188 |
| 4,298,685 | 11/1981 | Parikh et al. | 435/7 |
| 4,366,241 | 12/1982 | Tom et al. | 435/7 |
| 4,391,904 | 7/1983 | Litman et al. | 435/7 |
| 4,425,438 | 11/1984 | Bauman et al. | 436/527 |
| 4,435,504 | 3/1984 | Zuk et al. | 435/7 |
| 4,446,232 | 5/1984 | Liotta | 435/7 |
| 4,477,576 | 10/1984 | Deutsch et al. | 436/500 |
| 4,496,654 | 1/1985 | Katz et al. | 435/7 |
| 4,506,009 | 3/1985 | Lenhoff et al. | 435/7 |
| 4,533,629 | 8/1985 | Litman et al. | 435/7 |
| 4,540,659 | 9/1985 | Litman et al. | 435/7 |
| 4,632,901 | 12/1986 | Valkirs et al. | 435/5 |
| 4,703,017 | 10/1987 | Campbell et al. | 436/501 |
| 4,727,019 | 2/1988 | Valkirs et al. | 435/5 |
| 4,740,468 | 4/1988 | Weng et al. | 435/7 |
| 4,743,542 | 5/1988 | Graham, Jr. et al. | 435/7 |
| 4,778,751 | 10/1988 | El Shami et al. | 435/7 |
| 4,791,055 | 12/1988 | Boguslaski et al. | 435/7 |
| 4,803,170 | 2/1989 | Stanton et al. | 436/518 |
| 4,817,837 | 6/1974 | Rubenstein et al. | 195/63 |

THRESHOLD LIGAND-RECEPTOR ASSAY

DESCRIPTION

1. Field Of The Invention

This invention is in the field of ligand-receptor assays, including immunoassays, for the detection of selected analytes in a fluid sample. More particularly, this invention relates to methods for providing thresholds for signal production that are related to ligand concentrations in ligand-receptor assays. The inventive assays herein described may be used to obtain semi-quantitative determinations of one or more target ligand(s) in a single test format without the need for signal detection instrumentation. In these assay formats, the intensity of signal is directly related to ligand concentration in the sample.

2. Background Of The Invention

As used herein, the term "ligand-receptor" assay refers to an assay for an analyte which may be detected by the formation of a complex between a ligand and another substance capable of specific interaction with that ligand, i.e., ligand receptor. The ligand may be the analyte itself or a substance which, if detected, can be used to infer the presence of the analyte in a sample. In the context of the present invention, the term "ligand", includes haptens, hormones, antigens, antibodies, deoxyribonucleic acid (DNA), ribonucleic acids (RNA), metabolites of the aforementioned materials and other substances of either natural or synthetic origin which may be of diagnostic interest and have a specific binding partner therefor, i.e. the ligand receptor of the ligand-receptor assay. In the context of the present invention the term "ligand receptor" includes materials for which there is a specific binding partner, i.e. the ligand of the ligand-receptor assay. Those skilled in the art will appreciate that the analyte of interest, a member of a specific binding pair may be either ligand receptor or ligand depending upon assay design.

Ligand-receptor assays are generally useful for the in vitro determination of the presence and concentration of ligands in body fluids, food products, animal fluids, and environmental samples. For example, the determination of specific hormones, proteins, therapeutic drugs, and toxic drugs in human blood or urine has significantly improved the medical diagnosis of the human condition. There is a continuing need for simple, rapid, non-instrumental assays for the qualitative and semi-quantitative determination of such ligands in a sample. Furthermore, in many situations, such assays need to be simple enough to be performed and interpreted by non-technical users.

Ligand-receptor assays rely on the binding of ligands by receptors to determine the concentration of ligands in a sample. Ligand-receptor assays can be described as either competitive or non-competitive. Non-competitive assays generally utilize receptors in substantial excess over the concentration of ligand to be determined in the assay. Sandwich assays, in which the ligand is detected by binding to two receptors, one receptor labeled to permit detection and a second receptor frequently bound to a solid phase to facilitate separation from unbound reagents, such as unbound labeled first receptor, are examples of non-competitive assays. Competitive assays generally involve ligand from the sample, a ligand analogue labeled to permit detection, and the competition of these species for a limited number of binding sites provided by the ligand receptor. Those skilled in the art will appreciate that many variations of this basic competitive situation have been previously described and will not be discussed in detail herein except where pertinent to the general objectives of this invention. Examples of ligands which are commonly measured by competitive ligand-receptor assays include haptens, hormones and proteins. Antibodies that can bind these classes of ligands are frequently used in these assays as ligand receptors.

Competitive ligand-receptor assays can be further described as being either homogeneous or heterogeneous. In homogeneous assays all of the reactants participating in the competition are mixed together and the quantity of ligand is determined by its effect on the extent of binding between ligand receptor and labeled ligand analogue. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the enzyme is in the unbound state. Due to competition between unbound ligand and ligand-enzyme conjugate for antibody binding sites, as the ligand concentration increases the amount of unbound ligand-enzyme conjugate increases and thereby increases the observed signal. The product of the enzyme reaction may then be measured kinetically using a spectrophotometer.

In general, homogeneous assay systems require both an instrument to read the result and calibration of the observed signal by separate tests with samples containing known concentrations of ligand. The development of homogeneous assays has dominated competitive assay research and has resulted in several commercially available systems. Such systems are not, however, capable of providing results for the determination of multiple ligands in a sample in a single-test format not requiring instrumentation.

Heterogeneous, competitive ligand-receptor assays require a separation of bound labeled ligand or receptor from the free labeled ligand or receptor and a measurement of either the bound or the free fraction. Methods for performing such assays are described in U.S. Pat. Nos. 3,654,090, 4,298,685, and 4,506,009. Such methods, however, are not capable of providing semi-quantitative or quantitative results for the determination of ligands in a sample without using additional tests to calibrate the assay response.

The need for ligand-receptor assays that can be performed without the use of instrumentation has led to the development of immunoassays that are simple to perform and result in a response that can be visually interpreted. U.S. Pat. Nos. 4,125,372, 4,200,690, 4,246,339, 4,366,241, 4,446,232, 4,477,576, 4,496,654, 4,632,901, 4,727,019, and 4,740,468 describe devices and methods for ligand-receptor assays that develop colored responses for visual interpretation of the results. While such devices provide simple formats for the visual interpretation of assay results, only the presence or absence of ligand can be determined; semi-quantitative or quantitative determinations using these methods require that separate tests utilizing standards of known concentration be performed to establish the relationship between the observed response and the concentration of ligand.

Methods also have been developed for the internal calibration of ligand-receptor assays by providing devices that incorporate reference zones where the response at the reference zone represents the assay response for a particular concentration of ligand. The response generated by the unknown concentration of ligand in the sample at a test zone is compared with the response at the reference zone to determine the concentration of ligand in the sample either semi-quantitatively or quantitatively. European Patent Application No. 87302403.8 describes methods for using such internal references in non-competitive sandwich assays to provide semi-quantitative determinations from visual reading of the results and quantitative determinations from instrumental reading of the results. Likewise, U.S. Pat. No. 4,540,659 and European Patent Application No. 85307785.7 describe systems incorporating references that provide the ability to make semi-quantitative determinations in competitive ligand-receptor assays that are visually interpreted. Both of these systems provide a visual interpretation of the amount of labeled ligand analogue bound to solid phase immobilized receptor.

Employing the techniques described for competitive ligand-receptor assays, the intensity of the resulting color is inversely related to the concentration of ligand in the sample such that assay results that are more intense in color than the reference are interpreted to mean that the sample contained ligand at a lower concentration than that represented by the concentration by the reference. A serious drawback, however, to the widespread utilization of such visually interpreted, competitive ligand-receptor assays has been this inverse relationship between intensity of the developed signal and sample ligand concentration. This relationship provides that a sample with a low concentration of ligand will produce a large signal in the assay; and conversely a sample with a high concentration of ligand will produce a small signal in the assay. A further disadvantage of such assays is that if the requirement is for a single test to simultaneously determine multiple ligands each of which must be assigned a semi-quantitative value and each of which has specific individual concentration targets, then individual specific reference zones would have to be provided for each ligand to be determined. Under such circumstances, a test for multiple ligands becomes difficult to produce and complex to interpret.

Another prior art approach, a non-competitive immunochromatographic assay, is described in U.S. Pat. Nos. 4,168,146 and 4,435,504. This assay provides a method for quantitatively determining the presence of a single analyte in a sample in a visually interpreted immunoassay but does not permit the assay of multiple analytes without employing multiple devices. Furthermore, in practice this method is restricted to ligands whose sample concentrations are high relative to ligands that are commonly determined by competitive assay technology. Accordingly, this type of approach is of limited utility. Clearly, there is an unmet need for a ligand-receptor assay capable of determining the presence of a multiplicity of ligands in a sample and concurrently providing individualized semi-quantitative results for each ligand. Furthermore, such an assay should produce such results in a format that is simple enough for an non-technical user to correctly perform and interpret. The inventive assays of this invention meet these requirements.

The present invention is a method for performing competitive ligand-receptor assays so as to be able semi-quantitatively to determine the concentration of the ligand. The invention permits the identification and/or semi-quantitation of the target ligand to be carried out such that the ligand concentration is determined relative to an internally specified concentration, the threshold concentration. The threshold concentration can be arbitrarily pre-selected to be equivalent to any concentration appropriate to the ligand of interest. Furthermore, the present invention provides a method for performing competitive ligand-receptor assays for the simultaneous determination of a multiplicity of ligands, each determination including an internal threshold concentration specifically targeted for its respective ligand. One embodiment of the present invention is a method for performing competitive ligand-receptor assays for the simultaneous determination of a multiplicity of ligands, each determination including a compendium of internal threshold concentrations specifically targeted for the respective ligand. The method of the present invention affords the concentration determination to be carried out in a manner which is simple to employ and straightforward to interpret.

SUMMARY OF THE INVENTION

The present invention is directed to a ligand-receptor assay having three major elements and an additional optional element:

1) A reaction phase and mixture;
2) An optional means for removing selected species from the reaction mixture;
3) A terminal solid phase; and
4) A signal development phase.

The reaction phase comprises, in part, receptor for target ligand and ligand analogue conjugate. Ligand analogue conjugate comprises ligand analogue or ligand analogues bound to a signal development element. The ligand analogue portion of the ligand analogue conjugate is capable of competing with target ligand for the limited number of binding sites present on ligand receptor. A reaction mixture is formed from the sample and the reaction phase which includes ligand analogue conjugate and ligand receptor. The amounts of ligand receptor and ligand analogue conjugate are selected such that when the reaction mixture substantially approaches equilibrium binding conditions, substantially all of the ligand analogue conjugate is bound to ligand receptor when ligand is present at less than the threshold concentration. Subsequently, the reaction mixture is contacted with the next element of the ligand-receptor assay.

At this point, the reaction mixture can be contacted either with an optional means for removing ligand receptor from the reaction mixture, or can be immediately contacted with the terminal solid phase. Whether or not an optional means is necessary or desirable depends on a variety of factors, including the analytes of interest, their concentrations and the chosen assay format. The optional means can be used effectively, for example, in the assay of ligands in which the concentration range to be spanned is so large that a "hook" effect is possible. This disclosure describes specific assay formats employing an optional means. Other applications will be apparent to those skilled in the art. As used herein, the term "optional means" refers to a device or substance which may be operatively associated with (i.e., may complex to) a receptor directed against ligand receptor, i.e., a (ligand receptor) receptor. Thus, when the reaction mixture contacts the optional means, the (ligand receptor) receptor binds with all species associated with ligand receptor. In the reaction mixture this includes ligand receptor, ligand:ligand receptor complex and ligand analogue conjugate:ligand receptor complex. Alternatively, the optional means can be part of the reaction phase, or it can be introduced into the reaction mixture during the approach to equilibrium.

The reaction mixture is next contacted with the terminal solid phase. The terminal solid phase has non-diffusively immobilized ligand receptor capable of binding available ligand or ligand analogue conjugate. A portion of the ligand and ligand analogue conjugate not bound to ligand receptor in the reaction mixture then binds to the terminal solid phase immobilized ligand receptor. If necessary, the remainder of the reaction mixture may then be removed using a washing step. The washing step removes any ligand analogue conjugate which has not bound to ligand receptor immobilized on the terminal solid phase; thus, only ligand analogue conjugate bound to the terminal solid phase is left remaining.

The terminal solid phase which now contains ligand analogue conjugate:ligand receptor complex then is contacted with a signal development phase. The signal development phase enables the signal development element of the ligand analogue conjugate bound to the solid phase to produce a detectable signal. Interpretation of the detectable signal is such that the absence of a detectable signal indicates either that the target ligand is not present in the sample or that the target ligand is present in the sample at a concentration less than the threshold concentration. A detectable signal on the other hand, is indicative of the presence of the target ligand either at a concentration substantially equivalent to, or at a concentration greater than the threshold concentration.

DEFINITIONS

In interpreting the claims and specification, the following terms shall have the meanings set forth below.

Ligand - Binding partner to ligand receptor.

Ligand Analogue - A chemical derivative of the target ligand which may be attached either covalently or noncovalently to other species for example to the signal development element. Ligand analogue and ligand may be the same and both are capable of binding to ligand receptor.

Ligand Receptor - Receptor capable of binding ligand, typically an antibody, but which may be a ligand.

Ligand Analogue Conjugate - A conjugate of a ligand analogue and a signal development element.

Signal Development Element - The element of the ligand analogue conjugate which, in conjunction with the signal development phase, develops the detectable signal, e.g., an enzyme.

Threshold Concentration - The concentration of ligand in a sample which results in the first detectable signal development. A threshold concentration is an concentration reference point.

Reaction Phase - The phase normally containing the ligand analogue conjugate, e.g., hapten-enzyme conjugate, and ligand receptor, e.g., an antibody.

Reaction Mixture - The mixture of sample suspected of containing the target analyte and the reaction phase.

Ligand:Ligand Receptor Complex - The complex which occurs when ligand is bound by ligand receptor.

Ligand Analogue Conjugate:Ligand Receptor Complex - The complex which occurs when ligand analogue conjugate is bound by ligand receptor.

Optional Means - An optional means which is operatively associated with a receptor, e.g., an antibody which is capable of binding with selected components of the reaction mixture.

Terminal Solid Phase - The solid phase upon which the signal is finally developed during the signal development step.

Signal Development Phase - The phase containing the materials enabling the signal development element to develop signal, e.g., an enzyme substrate solution.

Ligand Complement - A specialized ligand used in labeling ligand analogue conjugates, receptors, ligand analogue constructs or signal development elements.

Ligand Complement Receptor - A receptor for ligand complement.

Ligand Analogue-Ligand Complement Conjugate - A conjugate composed of a ligand analogue, a ligand complement and a signal development element.

Reference Ligand - A ligand complement used to produce a reference ligand conjugate for use in providing a reference concentration point.

Reference Receptor - A receptor capable of binding with a reference ligand.

Reference Ligand Conjugate - A conjugate consisting of a reference ligand and a signal development element.

Reference Concentration - A reference concentration is developed using a reference ligand conjugate and a reference receptor. It is used in conjunction with the threshold concentration to define a range of concentrations.

Negative Control Ligand - A ligand complement used to produce a negative control ligand conjugate. A negative control ligand and (negative control ligand) receptor afford a means to insure the validity of an assay result.

(Negative Control Ligand) Receptor - A receptor capable of binding with a negative control ligand.

Ligand Receptor Conjugate - A conjugate of a ligand receptor and a signal development element.

Ligand Analogue Construct - A ligand analogue linked to a solid phase or to another molecule such that when bound to ligand receptor conjugate, ligand receptor conjugate is prevented from binding to immobilized ligand analogue on the terminal solid phase.

DETAILED DESCRIPTION OF THE INVENTION

Figure 1:
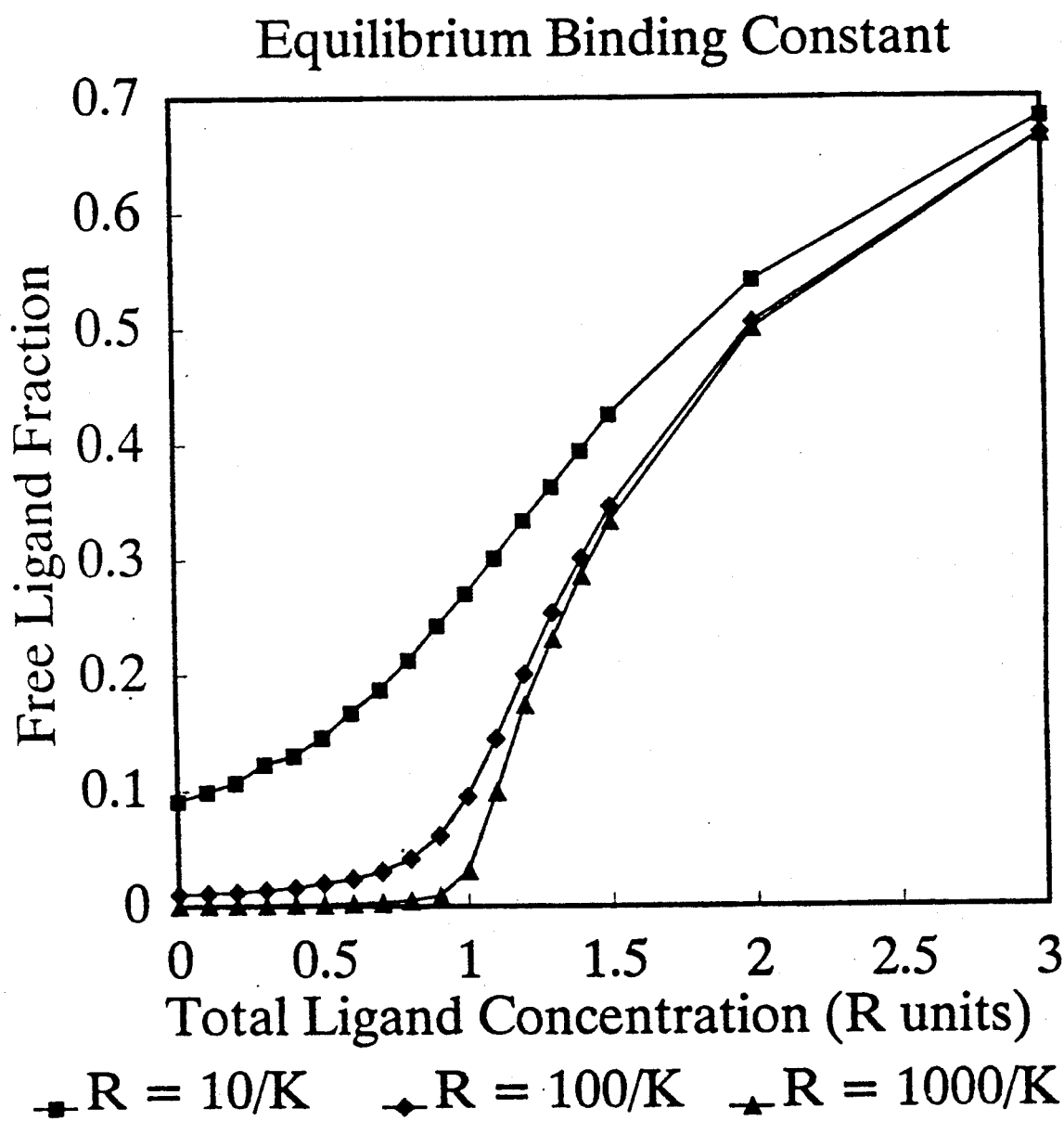
FIG. 1 is a graph showing the fraction of total unbound ligand as a function of total ligand. The graph shows that for a constant value of R, as the value of K increases, the functional form of a plot of free ligand as a function of total ligand concentration approaches a step function.

The aforementioned four elements of the ligand-receptor assays of the present invention, namely 1) a reaction phase and mixture; 2) an optional means for removing selected species from the reaction mixture; 3) a terminal solid phase; and 4) a signal development phase will be explained in detail in this section.

Reaction Phase And Mixture

The reaction phase normally contains both a ligand analogue conjugate comprised of a conjugate of a ligand analogue and a signal development element, and a ligand receptor. A preferred embodiment of the present invention employs ligand receptor in the reaction phase immobilized on a non-diffusive solid phase. In a particularly preferred embodiment of the present invention the ligand receptor is not immobilized on a non-diffusive solid phase and is thereby free to diffuse in solution.

Generally, methods for preparing the first reaction phase reagents of the present invention entail consideration of the following factors. Coupling of the ligand analogue to the signal development element to produce a ligand analogue conjugate must be accomplished such that recognition of the coupled ligand analogue by the ligand receptor directed against the uncoupled ligand is not substantially compromised. The number of ligands coupled to a signal development element must be sufficient to insure that the ability of ligand analogue conjugate to compete with ligand for binding sites on the ligand receptor is not substantially compromised. Similarly the number of ligand analogues coupled to a signal development element must not be so great as to substantially compromise the ability of ligand to compete with ligand analogue conjugate for binding sites on the ligand receptor. Preferred for the present invention are ligand analogue conjugates in which the number of ligand analogues coupled to the signal development element are between 1 and 50. Particularly preferred for the present invention are ligand analogue conjugates in which the number of ligand analogues conjugated to the signal development element are between 1 and 10.

A signal development element is an element which can produce a detectable signal. Those skilled in the art will recognize that many elements are capable of functioning as a signal development element, including without limitation, radionuclides, fluorescent species, phosphorescent species, chemiluminescent materials, dyes and enzymes. A preferred signal development element for the present invention is one which produces a signal capable of being detected by non-instrumental means. A particularly preferred signal development element is one which produces a signal capable of being detected by visual means, for example, an enzyme capable of reacting with an enzyme substrate in which the product of the enzymatic reaction is a molecule which absorbs electromagnetic radiation in the visible region of the electromagnetic spectrum.

Selection of ligand receptors to provide the complementary reagent for the ligand analogue conjugate must be accomplished with an understanding of the factors which control response function curves in competitive saturation ligand receptor assays. Some of these factors are discussed in R. P. Ekins, G. B. Newman and J. L. H. O'Riordan, *Theoretical Aspects of "Saturation" and Radioimmunoassay,* Radioisotopes in Medicine: In Vitro Studies, R. L. Hayes, F. A. Goswitz and B. E. P. Murphy, Eds. U.S. Atomic Energy Commission Oak Ridge, Tenn., 59-100 (1968), incorporated by reference herein. (All of the references hereinafter herein cited are hereby incorporated by reference). Of particular importance among such factors are the equilibrium binding constant of the ligand receptor for ligand and the width of the function describing the distribution of equilibrium binding constants for such an ensemble of ligand receptors. Preferred for use as ligand receptors in immunoassays are antibodies, particularly preferred antibodies for use as ligand receptors are monoclonal antibodies. Methods for generation of monoclonal antibodies are well known to those skilled in the art. Monoclonal antibodies can be readily developed with binding constants greater than $10^8$ $M^{-1}$ and due to monoclonality, antibody ensembles derived from a single cell line and directed against a specific ligand can be produced with a narrow distribution of equilibrium binding constants.

Ekins, et. al. have shown that the general form of the reaction which describes binding of a ligand by a ligand receptor selected from an ensemble of such ligand receptors may be represented by the expression

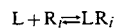
$$L + R_i \rightleftharpoons LR_i$$

where L represents the ligand and $R_i$ represents the binding site of the ith ligand receptor species with $i = 1, 2, 3, \ldots n$. The expression describing equilibrium binding is given as

$$K_i[L][R_i] = [LR_i]$$

Where $K_i$ is the equilibrium binding constant describing the reaction in which $R_i$ binds L. For the simplest case in which all $R_i$ have equal equilibrium binding constants, a closed solution for the expression can be obtained to relate the fraction of unbound ligand to the total amount of ligand for a fixed amount of receptor. This situation is of particular interest when the equilibrium binding constants, K, for binding of ligand to ligand receptor and for binding of ligand analogue conjugate to ligand receptor are substantially equivalent. The closed form solution for the simplest case in which all $R_i$ are equal is given by Ekins as $$(F_{f/b})^2 + F_{f/b}(1 - L/R - 1/KR) - 1/KR = 0$$

where $F_{f/b}$ is the ratio of free to bound ligand, L is the total concentration of ligand, R is the total concentration of ligand receptor binding sites and K is the equilibrium binding constant. Accordingly, the present invention shows that for a constant value of R, as the value of K increases, the functional form of a plot of free ligand as a function of total ligand concentration approaches that of a step function as illustrated in FIG. 1. The present invention further shows that the curvature at the step is related to the relationship between the equilibrium binding constant, K, and the total ligand receptor binding site concentration, R. In FIG. 1 the function plotted is the fraction of total ligand which is free (unbound) as a function of total ligand. For a constant value of R, as the value of K increases, it can be seen from FIG. 1 that a more dramatic step increase in free ligand fraction occurs. In the usual case, one selects ligand receptors of increasing equilibrium constant, K, to achieve a dramatic stepwise increase in the free ligand fraction. The relationship between free ligand fraction and the ratio of free to bound ligand, $F_{f/b}$, is given below $$L_f/L = F_{f/b}/(F_{f/b}+1).$$

Figure 2:
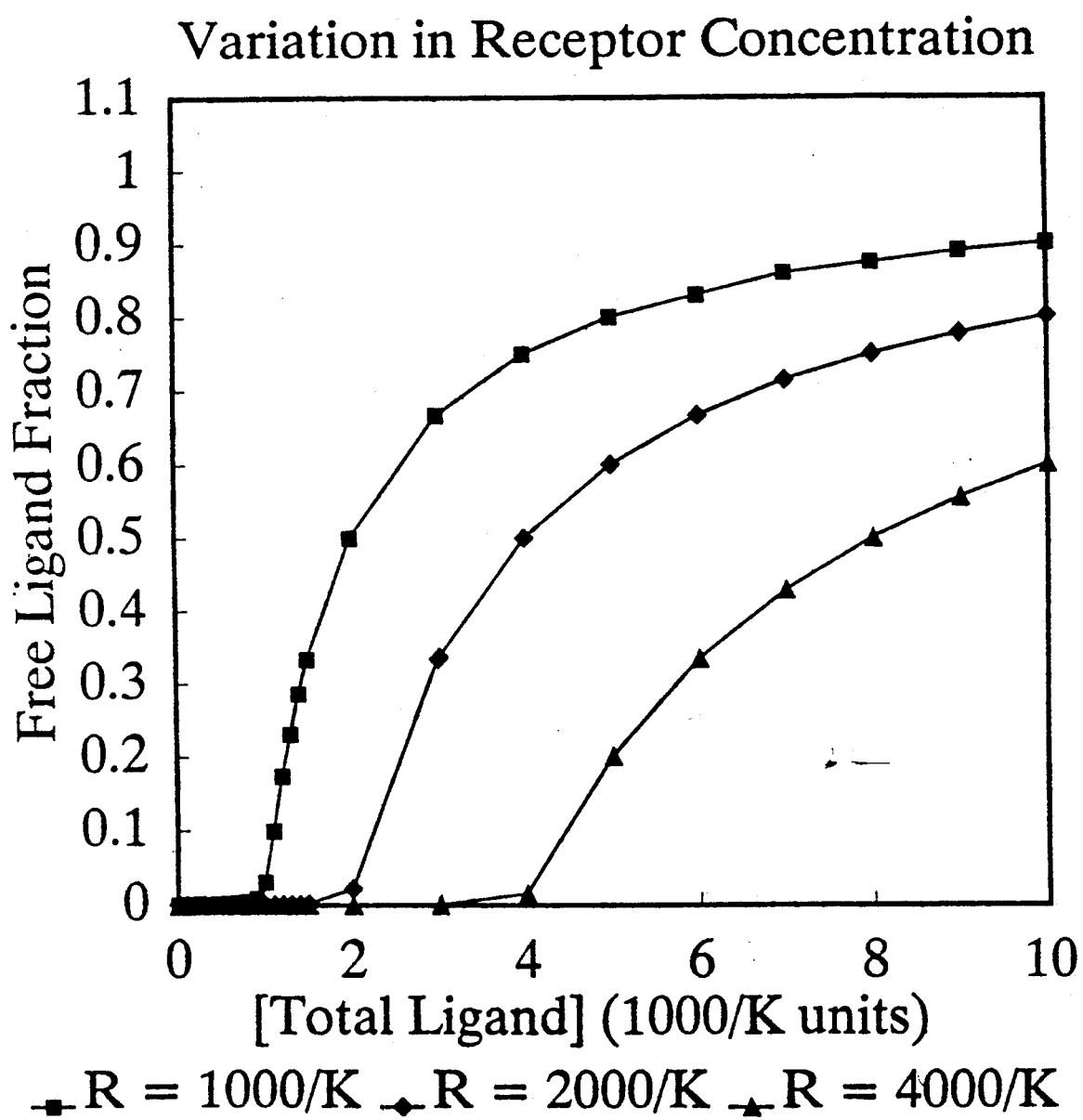
FIG. 2 is a graph showing the effect of the variation in ligand receptor concentration. The graph shows that increasing the value of R increases the ligand concentration corresponding to the position of the step.

The present invention makes use of these relationships and further extends this concept by showing that when R is sufficiently larger than 1/K, then the concentration position of the step is a function of the relative values of R. As is illustrated in FIG. 2, increasing the value of R increases the concentration corresponding to the position of the step.

In order to make use of these relationships in ligand receptor assays, ligand analogue conjugate and ligand receptor must be provided such that when contacted with sample in a reaction mixture, and after equilibrium binding has been substantially achieved, in the absence of ligand in the sample, substantially all of the ligand analogue conjugate is bound by ligand receptor. Those skilled in the art will appreciate that the amount of ligand receptor can be selected so that binding sites in excess of the number required to bind substantially all of the ligand analogue conjugate are provided in the reaction mixture. When the amount of ligand in the sample exceeds the amount of excess binding sites, then ligand and ligand analogue conjugate start to compete for available ligand receptor binding sites. The concentration of ligand in the sample that results in the first significant increase in the amount of unbound ligand analogue conjugate in the reaction mixture at substantially equilibrium binding is the threshold concentration. As illustrated in FIG. 2, the threshold concentration can be selected by appropriate choice of the concentration of ligand receptor in the reaction mixture. The application of this method to visual assays is of particular importance because the visible product of the assay response can be easily controlled so that no response is observed until the ligand exceeds its threshold concentration. As demonstrated by FIG. 1, the rate of increase of the unbound ligand analogue conjugate and the fraction of unbound ligand analogue conjugate when ligand is present at less than the threshold concentration are determined by the equilibrium binding constant and its relationship to the threshold concentration. Preferred for use as ligand receptors in the present invention are ligand receptors of equilibrium binding constant greater than $10^2 \times$(threshold concentration)$^{-1}$, particularly preferred for use are ligand receptors of binding constant greater than $10^3 \times$(threshold concentration)$^{-1}$.

The assay response described by the present invention was not achieved by the prior art. The prior art teaches that the free fraction of ligand analogue conjugate in the absence of ligand should be a significant fraction of the total ligand analogue conjugate in the assay in order to maximize sensitivity. In the present invention, substantially all of the ligand analogue conjugate is bound either in the absence of ligand or when the ligand concentration is less than the threshold concentration.

Figure 3:
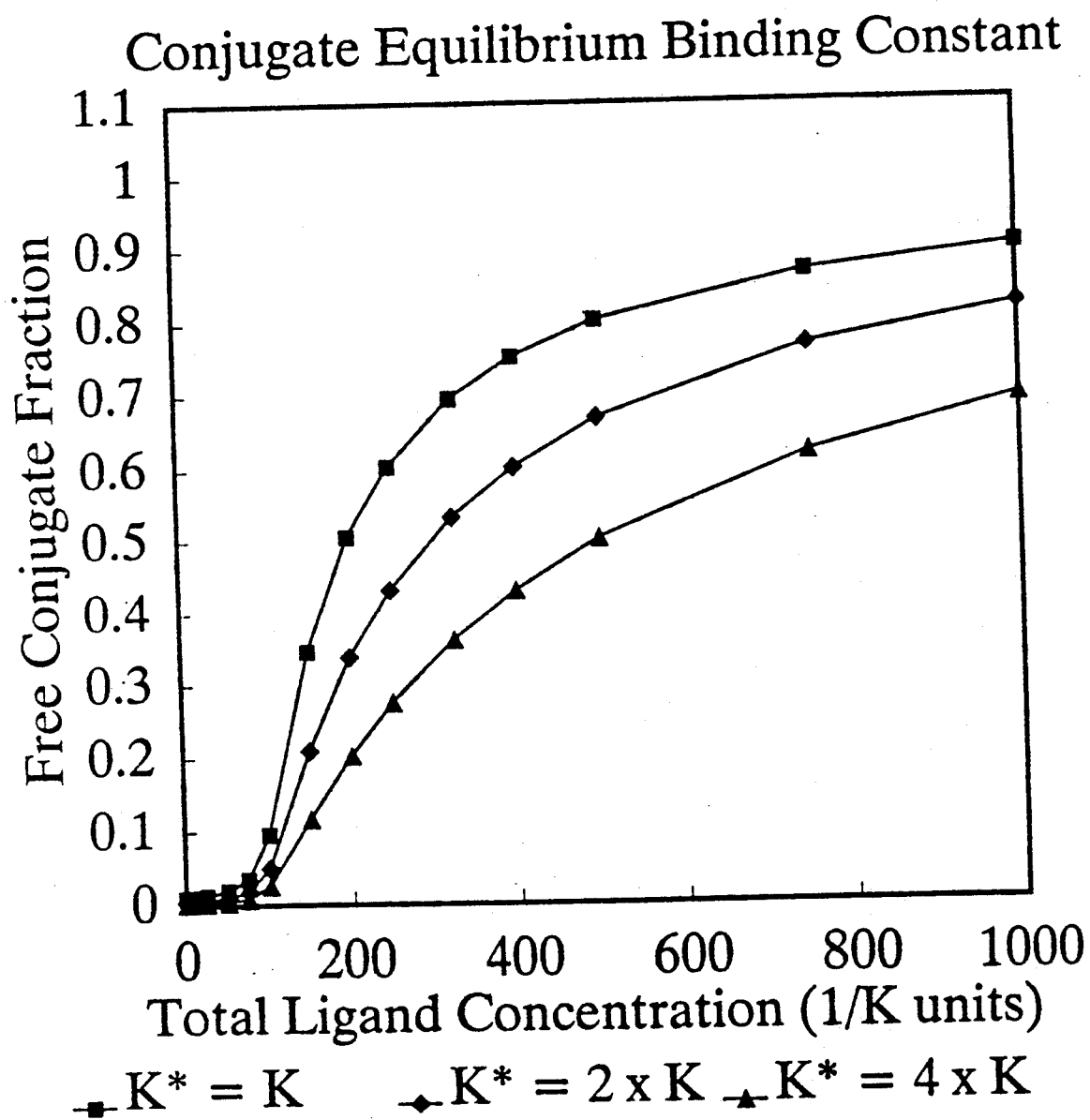
FIG. 3 is a graph showing the response function for ligand-receptor assays in which the equilibrium binding constants are not substantially equivalent for the binding of ligand to ligand receptor and for the binding of ligand analogue conjugate to ligand receptor. The concentration of receptor binding sites is 0.1 in units of 1/K.

The present invention is further directed to examples of ligand-receptor assays in which the equilibrium binding constants are not substantially equivalent for the binding of ligand to ligand receptor and for the binding of ligand analogue conjugate to ligand receptor. In particular, the present invention shows that the slope of the response function above the threshold concentration is determined by the magnitude of the equilibrium binding constant of the ligand receptor for the ligand analogue conjugate relative to the magnitude of the equilibrium binding constant of the ligand receptor for the ligand. When these binding constants are substantially equivalent, the response functions depicted in FIG. 1 describe the assay response. When the binding constants are not substantially equivalent, the response function varies as depicted in FIG. 3. When the magnitude of the equilibrium binding constant of the ligand receptor for the ligand analogue conjugate ($K^*$) is greater than the magnitude of the equilibrium binding constant of the ligand receptor for the ligand, the slope of the response function is reduced since more ligand is required to compete effectively with a given concentration of ligand analogue conjugate. Similarly, when the magnitude of the equilibrium binding constant of the ligand receptor for binding to ligand analogue conjugate is less than the magnitude of the equilibrium binding constant for binding to ligand the slope of the response function is correspondingly increased because less ligand is necessary to compete with a given concentration of ligand analogue conjugate.

Therefore, the slope of the response function can be varied by varying the magnitude of the equilibrium binding constant of the ligand receptor for ligand analogue conjugate. This variation is most readily achieved in practice by varying the number of ligand analogues per signal development element. Conjugates with higher ratios of ligand analogue to signal development element exhibit larger magnitude equilibrium binding constants for binding with the ligand receptor and have response functions that have correspondingly reduced slopes relative to conjugates less derivatized with ligand. Ligand analogues can be coupled by different means to signal development elements to change their equilibrium binding constants for ligand receptor. Thereby, one can design ligand analogues that exhibit larger or smaller magnitude equilibrium binding constants than does the ligand for the ligand receptor. The ability to empirically adjust the slope of the response function is beneficial in optimizing assays.

For example, in the present invention, the preferred method for performing threshold immunoassays (as described herein) utilizes soluble antibody and a ligand analogue conjugate in a reaction phase to which is added a sample potentially containing target ligand. This mixture is allowed to come substantially to conditions of equilibrium binding. In the absence of target ligand, substantially all of the ligand analogue conjugate is bound to antibody and is not available for binding to antibody immobilized on the terminal solid phase.

The reaction phase can be provided in many ways. The correct relative and absolute amounts of ligand analogue conjugate and antibody must be provided in order to pre-establish a threshold concentration of target ligand below which little or no signal is developed. One method is to mix a fixed sample volume with a fixed amount of ligand analogue conjugate, add this mixture to a fixed amount of antibody, and allow the final mixture to come substantially to conditions of equilibrium binding. A second method is to add a fixed sample volume to a fixed antibody volume and then add a fixed amount of ligand analogue conjugate. A third method is to add sample to a mixture of ligand analogue conjugate and antibody. If antibody and ligand analogue conjugate have been allowed to react prior to the addition of ligand from the sample, the dissociation of the ligand analogue conjugate:antibody complex becomes the rate limiting step governing the approach to conditions of equilibrium binding. For large ligand analogue conjugates this can prove to be an unacceptably long period of time for most applications.

One practical consideration is the expense of the antibody and ligand analogue conjugate reagents. For ligands in which the threshold concentration is desired to be 1 $\mu$M or greater, the cost of the reagents may become significant and therefore, the reagent volumes should be small to produce a cost effective assay kit. In order to address this consideration, a preferred method for providing the antibody and ligand analogue conjugate reagents is to co-lyophilize them without permitting them to react with one another. Such a process can be accomplished by adding the correct volume of the first reagent to a vial and freezing it, followed by the addition of the correct volume of the second reagent to the vial with rapid freezing to avoid melting of the first reagent and thereby possible mixing of the two reagents. The two frozen reagents are then co-lyophilized.

Accordingly, the present invention affords a ligand receptor assay process which includes a step function-like element in the assay response function curve and concurrently provides a mechanism for associating the position of the step with a specific selected ligand concentration, the threshold concentration, which is selectable by adjustment of the relative values of the concentrations of the ligand analogue conjugate and the ligand receptor.

Optional Means For Removal Of Ligand Receptor From Reaction Mixture

An optional means for removing ligand receptors from the reaction mixture may be included whenever it is necessary or desirable to prevent ligand analogue conjugate: ligand receptor complexes in the reaction mixture from contacting the terminal solid phase. Such an optional means is necessary if, for example, ligand analogue conjugate:ligand receptor complex in the reaction mixture dissociates to a significant extent during incubation with the terminal solid phase such that terminal solid phase immobilized ligand receptor could bind dissociated ligand analogue conjugate and result in a detectable signal even in the absence of target ligand. The optional means for removing ligand receptors from the reaction mixture may be any device means for binding ligand receptors so that they are removed from the reaction mixture prior to contacting the reaction mixture with the terminal solid phase. For example, such an optional means may consist of (ligand receptor) receptors and solid phase supports for immobilization of these (ligand receptor) receptors, such that through binding of reaction mixture ligand receptors to (ligand receptor) receptors immobilized on the solid phase support of the optional means, the ligand receptors and ligand receptor associated complexes are prevented from contacting ligand receptors bound to the terminal solid phase. Examples of receptors and solid phases which may be useful in constructing optional means for the removal of ligand receptors include anti-antibody antibodies such as goat-anti-mouse IgG or goat-anti-mouse Fc, receptors such as protein A and protein G, and solid phases such as diffusible beads, macroporous agarose beads, membranes, filters, and porous matrices. Alternatively, ligand complement receptors immobilized on solid phases may be used to remove ligand receptors labeled with ligand complement from the reaction mixture, e.g. ligand receptors labeled with biotin can be bound by avidin immobilized on solid phases. Ligand receptors also can be precipitated from the reaction mixture using a (ligand receptor) receptor. When beads are used as the solid phase, receptors for ligand receptors are normally immobilized on the beads and the beads may be added to the reaction mixture as part of the reaction phase, during the incubation of the reaction mixture, or after the reaction mixture has substantially achieved equilibrium binding. Centrifugation or filtration may be necessary to remove the beads from the reaction mixture prior to contact with the terminal solid phase. When porous matrices, including membranes and filters, are used as the solid phase, the reaction mixture can be contained within the porous matrix or the reaction mixture can be introduced to the porous matrix after conditions of equilibrium binding have been substantially approached. In either case the porous matrix functions to remove ligand receptors and their complexes prior to contact with the terminal solid phase.

Terminal Solid Phase

The terminal solid phase is a solid support having localized ligand receptors for target ligands and ligand analogue conjugates. The terminal solid phase of the invention may be a solid support onto which are localized ligand receptors in distinct loci capable of binding both target ligands and ligand analogue conjugates. In the context of the present invention, the term "localized" encompasses all physical mechanisms for immobilizing receptors such that during the performance of the ligand-receptors receptor assay process substantially all of the receptor remains in a pre-determined locus. Such mechanisms include covalent binding, noncovalent binding, chemical coupling, physical entrapment of particulates operatively associated with receptors, and adsorption by hydrophobic/hydrophobic or hydrophilic/hydrophilic interactions. The localization of the ligand receptor onto the solid support of the solid phase of the present invention may be accomplished in a number of ways. The ligand receptor may be localized by the technique of entrapping ligand receptor coated particulates by a porous matrix solid support. Methods for introducing said particulates to a porous matrix are discussed in U.S. Pat. Nos. 4,446,232, 4,740,468 and European Patent Application 86302521.9, incorporated by reference herein. A particularly preferred method of localization of the ligand receptor onto the solid support wherein the solid support is a porous matrix comprises in part, localization of the ligand receptor on the solid support by covalent or non-covalent chemical binding. Techniques for binding ligand receptors to a solid support are well known in the art. A variety of solid supports, including a porous matrix, a non-porous matrix, beads, membranes or filters, may be used in the present invention. Such solid supports can be incorporated into a variety of test devices including dipsticks and devices such as those described in U.S. Pat. Nos. 4,200,690, 4,246,339, 4,366,241, 4,632,901, and 4,727,019. A particularly preferred solid phase is a membrane suspended in a device such that when the reaction mixture is contacted with the membrane, the reaction mixture is of sufficient volume to completely fill the void volume of the exposed membrane such that the total surface area of the membrane and all receptor zones are contacted by the reaction mixture. Such a device would also incorporate, if necessary, a means for removal of unbound conjugates from the membrane and a means for contacting the signal development phase with conjugates bound to immobilized receptors on the membrane.

Clearly the use of the method of the present invention with such devices would provide one with the ability to assay for multiple analytes in a single sample using a single test device which will provide threshold immunoassay results for each analyte. In the multiple simultaneous ligand assay formats a solid support comprising for each ligand to be determined, at least one discrete reaction zone on which is localized one said ligand receptor may be used. Furthermore, the incorporation of internal negative controls and positive references will add to the information provided by the assay result.

Furthermore, the preferred terminal solid phase as described above is particularly useful where it is highly desirable to simultaneously determine the presence of more than one ligand of interest, such as for the determination of causative agents of a toxicological response. This may be readily accomplished by binding of ligand receptors within discrete zones of the support matrix. Such a solid phase system provides, in essence, a panel of ligand receptors capable of screening for toxins which may be present in a patient fluid sample. Accordingly the pattern of reactivity on the solid phase system, as determined by the presence of bound toxin analogue conjugates, provides an indication of the nature of the toxins eliciting the toxicological response.

Therefore, in one of the embodiments of the present invention, the reaction mixture which may contain in part, ligand, ligand analogue conjugate, ligand receptor, ligand:ligand receptor complex and ligand analogue conjugate:ligand receptor complex is contacted with a terminal solid phase upon which is immobilized ligand receptor. In a preferred embodiment the terminal solid phase is composed of a non-diffusible bead, membrane or filter upon which the receptor is immobilized. In a particularly preferred embodiment, the terminal solid phase is composed of a porous matrix upon which the ligand receptor is immobilized. The ligand receptor can be immobilized by a variety of methods including but not limited to direct covalent chemical attachment, indirect covalent chemical attachment, direct non-covalent chemical attachment, indirect non-covalent chemical attachment and physical entrapment. In a preferred embodiment the ligand receptor immobilized on the terminal solid phase is capable of binding with ligand analogue conjugate. Furthermore, in a preferred embodiment for application of the present invention to immunoassays the ligand receptor is an antibody. In a particularly preferred embodiment the ligand receptor immobilized on the terminal solid phase is identical to the ligand receptor which is included in the reaction phase mentioned above which first contacts the sample. In another particularly preferred embodiment for application of the present invention to immunoassays, the ligand receptor is a monoclonal antibody.

Signal Development Phase

The signal development phase is a phase which enables the signal development element to produce a detectable signal. Elements of the signal development phase may exist in any or all of the following assay components, the reaction phase, the optional means, the terminal solid phase, and the signal development phase. Preferred for use as components of the signal development phase are materials which enable the signal development phase to produce a signal which is detectable by non-instrumental means. Particularly preferred for use as components in the signal development phase are materials which enable the signal development element to produce a signal detectable by visual means. Those skilled in the art will appreciate that a variety of materials can be used to accomplish this end, by way of example the following is offered; an enzyme substrate solution, e.g., 3-indoxyl phosphate, which when contacted with the terminal solid phase containing bound enzyme is converted by the enzyme, e.g., calf intestinal alkaline phosphatase (E.C. 3.1.3.1), to a visible, blue-colored reaction product, indigo. Another example of a signal development phase comprises channeling methods as described in U.S. Pat. No. 4,233,402 when used in conjunction with a terminal solid phase as described in U.S Pat. No. 4,391,904. Such methods substantially eliminate the need to remove unbound conjugates by a washing mechanism; they are preferred as the signal development phase of this invention.

Ligand-Receptor Assay Process

To begin the ligand-receptor assays of the present invention one introduces a fluid sample suspected of containing a target ligand to the reaction phase of ligand analogue conjugate and ligand receptor. Competition occurs between the ligand analogue conjugate and the target ligand for the limited number of binding sites available on the ligand receptor. The relative amounts of ligand analogue conjugate and ligand receptor are such that in the absence of target ligand, and subsequent to the achievement of substantially equilibrium binding, substantially all of the available ligand analogues on the ligand analogue conjugate are bound. One skilled in the art will appreciate that for fixed amounts of ligand analogue conjugate and ligand receptor that the volume of the sample can be varied to vary the threshold concentration. Significant amounts of unbound ligand analogue conjugate are not present unless the sum of the effective concentration of ligand analogue on the ligand analogue conjugate and the concentration of target ligand begins to exceed the concentration of available ligand receptor binding sites. As used herein, the term "unbound" means a conjugate having at least one available ligand analogue capable of binding to ligand receptor. The ligand analogue conjugate may have more than one ligand analogue and may have ligand receptor bound to it, nevertheless, as long as it has at least one additional available ligand analogue capable of binding to ligand receptor it may be termed "unbound". "Bound" ligand analogue conjugates are those which do not have any ligand analogues available for binding. It should be understood that the effective concentration of ligand analogue conjugate is dependent on the number of antibody binding sites that can be bound to a single conjugate molecule. Therefore, heavily derivatized conjugates containing many ligand analogues will have higher ligand analogue concentrations than less derivatized conjugates. The concentration of ligand which results in the first significant increase in unbound ligand analogue conjugate is the threshold concentration. As the amount of ligand increases above the threshold concentration, the amount of ligand analogue conjugate not bound to ligand receptor also increases. The increase in the amount of unbound ligand analogue on the ligand analogue conjugate continues until the amount of target ligand has increased to such a value that substantially all of the ligand analogue conjugate exists in a state in which it is unbound to ligand receptor.

In a preferred embodiment of the present invention the ligand receptor in the reaction phase is not non-diffusively immobilized and is therefore capable of diffusive motion during the competition reaction for ligand receptor binding sites which occurs between ligand and ligand analogue conjugate. In a particularly preferred embodiment, the target ligand and the ligand analogue conjugate participate in a competition for binding sites on the diffusible ligand receptor. In a particularly preferred embodiment, the present invention provides a process for an immunoassay in which the ligand receptor is a monoclonal antibody free to diffuse in solution. The reaction mixture contains in part, ligand, ligand analogue conjugate, ligand receptor, ligand:ligand receptor complex and ligand analogue conjugate:ligand receptor complex. Subsequent to the competition reaction the reaction mixture is then contacted with an optional means operatively associated with a (ligand receptor) receptor. The optional means associated (ligand receptor) receptor binds to all species associated with ligand receptor. Accordingly, the optional means associated (ligand receptor) receptor can bind to ligand receptor, ligand:ligand receptor complex and ligand analogue conjugate:ligand receptor complex from the reaction mixture. Removal of ligand receptor associated components from the reaction mixture by the optional means allows only the unbound ligand analogue conjugate to be contacted by the terminal solid phase immobilized ligand receptor. Thus, when an optional means is used to remove ligand receptor and moieties bound to ligand receptor from the reaction mixture, the unbound ligand analogue conjugate in the reaction mixture refers to ligand analogue conjugate that is not bound to ligand receptor.

The reaction mixture is then contacted with the terminal solid phase upon which is immobilized ligand receptor. Accordingly, the present invention provides a process where the ligand receptor is immobilized on a solid phase. Preferred solid phases for use in immobilizing the receptor include diffusible beads, membranes and filters. Particularly preferred for use as the solid phase for immobilization of the receptor is a porous matrix. The ligand receptor immobilized on the terminal solid phase contacts the components of the reaction mixture, which consist in part of, unbound ligand, and unbound ligand analogue conjugate. If the reaction mixture has not been contacted with an optional means the reaction mixture also may contain uncomplexed ligand receptor, ligand:ligand receptor complex and ligand analogue conjugate:ligand receptor complex. When the reaction mixture has not been contacted with an optional means, unbound ligand analogue conjugate refers to ligand analogue conjugates that are capable of binding to immobilized ligand receptors on the terminal solid phase even though ligand receptors from the reaction mixture already may be bound to some ligand analogues on the ligand analogue conjugate. A competition occurs between any unbound ligand and any unbound ligand analogue conjugate for available binding sites on the ligand receptor immobilized on the terminal solid phase. After allowing binding reactions to proceed, the terminal solid phase and the reaction mixture may be separated. Any ligand analogue conjugate which has not bound to the ligand receptor immobilized on the terminal solid phase is removed if necessary, by a separation step. The ligand analogue conjugate complexed with the ligand receptor immobilized on the terminal solid phase is contacted with a signal development phase which enables the signal development element of the complexed ligand analogue conjugate to develop a detectable signal. Interpretation of the signal is such that absence of a detectable signal indicates that the target ligand is at a concentration in the sample lower than the threshold concentration, while presence of a detectable signal indicates that the target ligand is either at a concentration substantially equivalent to or at a concentration greater than the threshold concentration.

Negative Control Ligand

The reaction mixture of the present invention should be allowed to come substantially to equilibrium prior to contact with the terminal solid phase so that in the presence of target ligand at less than the threshold concentration, the ligand analogue conjugate is bound substantially completely by ligand receptor in the reaction mixture and cannot bind to immobilized ligand receptor on the terminal solid phase. In order to determine that the reaction mixture has properly approached equilibrium and subsequent assay results are valid, a preferred method for practicing this invention is the inclusion of a negative control ligand conjugate. The negative control ligand is a ligand not normally found in samples. The combination of negative control ligand conjugate, ligand analogue conjugate, ligand receptor and (negative control ligand) receptor is provided such that when the assay is performed properly, no response is observed at the (negative control ligand) receptor locus on the terminal solid phase because the reaction mixture has substantially achieved equilibrium binding conditions where substantially all of the negative control ligand conjugate is bound by (negative control ligand) receptors in the reaction mixture. If insufficient time is allowed for the reaction mixture to substantially approach equilibrium or if the signal development phase is incorrectly performed, responses may be observed at the ligand specific test loci that falsely indicate the presence of target ligands at greater than the threshold concentrations. Under these circumstances, the negative control locus would also exhibit an observable response and would indicate that the test is invalid. Such a negative control provides assurance that the assay protocol has been performed correctly and confirms the validity of any positive results. Ligands which are useful as negative control ligands may be selected from the same general class of ligands not normally present in samples of interest (i.e., ligand complements) but which can be used to generate ligand complement conjugates and ligand complement receptors which exhibit the appropriate affinity for the ligand. Such ligands include, for example, fluorescein.

Use Of Threshold Concentration And Reference Point To Determine Concentration Range Of Ligand A preferred method of this invention utilizes a threshold concentration to define the lower limit of a concentration range for a target ligand and a reference point to determine the upper limit of that concentration range. The reference response is at a locus distinct from the locus of the test response and is further chosen to represent the response produced by a target ligand concentration corresponding to the upper limit of the concentration range. The response at the reference locus can be provided by a ligand-receptor pair in which the reference receptor is immobilized at the reference locus and the reference ligand is labeled with a signal development element to permit detection, for example, using a reference ligand conjugate. Ligands which are useful for such purposes are ligands that are not normally found in samples of interest, i.e., ligand complements, so that no competition occurs between reference ligand conjugate and target ligand for either reference receptor or ligand receptor binding sites. Ligands such as fluorescein are useful as reference ligands for this purpose and fluorescein-labeled enzymes are useful as reference ligand conjugates in conjunction with anti-fluorescein antibodies as reference receptors for the purpose of providing a reference response to determine whether the assay response at the test locus corresponds to a ligand concentration that is less than or substantially equivalent to or greater than the upper limit of the concentration range.

Alternatively, the signal development element itself could function as the reference ligand conjugate, e.g., enzyme could be used with an anti-enzyme antibody as the reference receptor. Since the slope of an assay response function can be selected by adjusting the degree of derivatization of the ligand analogue conjugate, the assay response function can be optimized in order to extend the full dynamic range of the assay response function over the selected range of target ligand concentrations. This approach affords the maximum ability to assess whether the concentration of target ligand is above, below, or within the selected concentration range. No signal development in the test locus indicates that the sample contains target ligand at less than the lower limit of the concentration range. Detectable signal development which is less than the reference response indicates that the sample contains target ligand at a concentration within the selected concentration range. Assay responses substantially equivalent to or greater than the reference response indicate that the sample contains target ligand at concentrations above the selected concentration range. The use of references that represent pre-determined concentrations of ligands in competitive assays have been described in U.S. Pat. No. 4,540,659 and European Patent Application 85307785.7. However, these applications would require two such reference points to determine a concentration range. By necessity, these methods compress the dynamic range of assay response which one could use for the range of selected ligand concentrations. For this reason, the method of the present invention for utilizing such references is a significant improvement for performing such competitive ligand-receptor assays in which the concentration of the ligand is determined relative to two pre-determined ligand concentrations. The method of the present invention is of particular utility in determining ligand concentration relative to a selected concentration range.

Ligand Receptor Assay Process For A Ligand Utilizing Ligand Analogue-Ligand Complement Conjugate In another embodiment of the ligand-receptor assays of this invention, the ligand analogue conjugate is augmented by the inclusion of a specialized ligand, termed a ligand complement. The ligand complement is a ligand not normally found in samples to be tested. The inclusion of a ligand complement creates a conjugate with both ligand analogue and ligand complement bound to the signal development element. A fluid sample is contacted with a reaction phase having a complementary reaction pair of ligand analogue-ligand complement conjugate and ligand receptor for the target ligand of interest. The ligand receptor may be an antibody immobilized on a solid phase. The target ligand and the ligand analogue-ligand complement conjugate compete for binding sites on the solid phase immobilized ligand receptor. If the target ligand is present at less than the threshold concentration, substantially all of the ligand analogue-ligand complement conjugate is bound to ligand receptor. In a particularly preferred embodiment the ligand receptor is a monoclonal antibody free to diffuse through the reaction mixture. When the ligand receptor is free to diffuse in the reaction mixture, an optional means for removing ligand receptors from the reaction mixture is needed prior to contacting the terminal solid phase containing immobilized ligand complement receptor. The inclusion of a ligand complement in the ligand analogue conjugate eliminates the potential "hook" effect problem.

In certain assay formats, a hook effect may occur when the remaining amount of unbound ligand which contacts the terminal solid phase is so large that it efficiently competes with unbound ligand analogue conjugate for binding sites on the immobilized ligand receptor. When the competition greatly favors binding of target ligand, then the signal developed by any ligand analogue conjugate:ligand receptor complexes formed on the terminal solid phase may be so small as to be undetectable. The assay would then be incorrectly interpreted as indicating that the concentration of the target ligand in the sample was below the threshold concentration. In the present invention, using a terminal solid phase containing an immobilized receptor which is directed against a complement ligand (i.e., a ligand complement receptor) can overcome this limitation. When the reaction mixture is placed in contact with a terminal solid phase having an immobilized ligand complement receptor, no competition occurs between remaining target ligand and ligand analogue-ligand complement conjugate for binding sites on the immobilized ligand complement receptor. Under these circumstances binding of ligand analogue-ligand complement conjugate will be both maximal and unaffected by residual target ligand. A hook effect will not occur and the target ligand concentration may be correctly interpreted. Therefore, following contact of the terminal solid phase with a signal development phase, absence of a detectable signal indicates the ligand to be at a concentration less than the threshold concentration, while presence of a detectable signal indicates the presence of ligand at a concentration substantially equivalent to or greater than the threshold concentration.

Ligand-Receptor Assay Process For The Simultaneous Determination Of Multiple Ligands The present invention is particularly useful in the performance of simultaneous multiple ligand-receptor assays. Any number of non-interacting complementary ligand analogue conjugate:ligand receptor reaction pairs can be employed concurrently to determine multiple target ligands of interest in a single sample.

In the assays of the present invention, a fluid sample suspected of containing target ligands of interest is contacted with a reaction phase containing complimentary ligand analogue conjugate :: ligand receptor reaction pairs in a number equal to the number of target ligands to be determined. A competition occurs between target ligands and their respective ligand analogue conjugates for binding sites on the complementary ligand receptor. The multiple non-interacting competitive reactions all are allowed to approach substantially equilibrium binding conditions. At equilibrium for each of the competitive systems the amount of unbound ligand analogue conjugate will be determined by a number of factors, of particular importance being the amount of the respective target ligand present in the sample. In the absence of the specific target ligand, essentially all of the respective ligand analogue conjugate will be bound by the appropriate ligand receptor. At equilibrium, significant amounts of the specific ligand analogue conjugate will only be present when the target ligand concentration is substantially equivalent to or greater than the respective threshold concentration. To detect the presence of specific ligands at or above their respective threshold concentrations, the reaction mixture is contacted with a terminal solid phase containing discrete zones of immobilized ligand receptors for the respective ligands and a signal development phase in order to determine which if any of the ligands were present at or above their threshold concentrations.

Furthermore, since each ligand receptor immobilized on the terminal solid phase is placed in a discrete locus or loci, the signal produced by the signal development element of an immobilized ligand analogue conjugate can be uniquely associated with a specific target ligand. The one-for-one association of detectable signal with ligand is achieved by correlating signal location with the positional identification of specific ligand receptors. The present invention, therefore, affords the concentration of a multiplicity of target ligands to be simultaneously assessed, each with respect to an individually preselected threshold concentration, such that the absence of a detectable signal in a ligand-specific reaction zone on the terminal solid phase indicates that the specific target ligand is present in the sample at a concentration less than the ligand-specific threshold concentration, while the presence of a detectable signal in a ligand-specific reaction zone on the terminal solid phase indicates that the specific ligand is present in the sample either at a concentration substantially equivalent to or greater than the ligand-specific threshold concentration.

Ligand-Receptor Assay Process For The Simultaneous Determination Of Multiple Ligands With Multiple Threshold Concentrations For Each Ligand One of the embodiments of this invention is a ligand-receptor assay for a multiplicity of target ligands in which the reaction phase includes groups of complementary reagents, each group having multiple ligand analogue-ligand complement conjugates and an appropriate ligand receptor. The ligand analogue-ligand complement conjugates are constituted in proportions relative to the complementary reaction phase ligand receptor, such that at the complexation step with their respective terminal solid phase immobilized ligand complement receptors, signal development occurs so that each complementary ligand analogue-ligand complement conjugate :: immobilized ligand complement receptor pair exhibits a unique threshold concentration for the commonly shared target ligand. The compendium of threshold concentrations for a single target ligand provides a mechanism for further identifying the concentration of the target ligand by comparison with the range of threshold concentrations. Since the reaction phase includes a multiplicity of groups of complementary reagent pairs, a multiplicity of target ligands may be simultaneously determined, each ligand having an associated series of threshold concentrations. Thereby in this fashion, each target ligand can be bracketed into one of a series of concentration ranges. Examples of such uses of ligand analogue-ligand complement conjugates to determine multiple analytes at multiple threshold levels include the use of ligand analogue-ligand complement conjugates in which the ligand complement component of the conjugate is sterically hindered from binding to the terminal solid phase ligand complement receptor upon the complexation of ligand receptor with the ligand analogue component of the ligand analogue-ligand complement conjugate. Such conjugates are described in U.S. Pat. No. 4,506,009. A reaction mixture which includes sample, ligand receptor and ligand analogue-ligand complement conjugate is allowed to substantially approach equilibrium. The reaction mixture is then contacted with a terminal solid phase upon which is localized ligand complement receptor. Ligand analogue-ligand complement conjugate:ligand receptor complex cannot be bound by terminal solid phase immobilized ligand complement receptor since the conjugate complex has an effective ligand complement concentration of zero. Unbound ligand analogue-ligand complement conjugate can be bound by the immobilized ligand complement receptor and following any necessary free/bound separation steps and contact with a signal development phase, the ligand concentration can be determined relative to the threshold concentration. When multiple ligand complement receptors are immobilized at specific loci on the terminal solid phase, each locus is identified with a unique threshold concentration such that the presence of a detectable signal at a locus indicates that the ligand is present in the sample at a concentration substantially equivalent to or greater that the corresponding threshold concentration.

Another example involves using a ligand analogue-ligand complement conjugate in the reaction mixture and the use of an optional means. A reaction mixture is formed from a sample, ligand receptor and a ligand analogue-ligand complement conjugate. The competition reaction between ligand and ligand analogue-ligand complement conjugate for the limited binding sites on the ligand receptor is allowed to substantially approach equilibrium. The reaction mixture then is contacted with an optional means operatively associated with a (ligand receptor) receptor which can bind to those components of the reaction mixture associated with ligand receptor, that is, unbound ligand receptor, ligand:ligand receptor complex, and ligand analogue-ligand complement conjugate:ligand receptor complex. The resulting reaction mixture then is contacted with a terminal solid phase upon which is immobilized ligand complement receptor. A portion of the unbound ligand analogue-ligand complement conjugate remaining in the reaction mixture is bound by the terminal solid phase immobilized ligand complement receptor and the remainder may be removed, if necessary, in a separation step. Finally, the terminal solid phase is contacted with a signal development phase and the ligand concentration is determined relative to the threshold concentration. When multiple ligand complement receptors are immobilized at specific loci on the terminal solid phase, each locus is identified with a unique threshold concentration such that the presence of a detectable signal at a locus indicates that the ligand is present in the sample at a concentration substantially equivalent to or greater that the corresponding threshold concentration.

Ligand-Receptor Assay Using Receptor Conjugate And Ligand Analogue Construct One skilled in the art will appreciate that a receptor conjugate and a ligand analogue construct can be used in a reaction mixture to provide threshold concentrations for the determination of target ligands in ligand-receptor assays. Substantially all of the receptor conjugate is bound to ligand analogue construct and is prevented from binding to a terminal solid phase containing immobilized ligand analogue when the target ligand is present at less than the threshold concentration. Receptor conjugates containing multiple ligand binding sites are preferred for use in this embodiment. A ligand analogue construct can be formed by binding ligand analogue to an optional solid phase as a means for separating receptor conjugate from the reaction mixture. Alternatively, ligand analogue constructs can be formed by binding ligand analogues to large molecular species which will prevent receptor conjugates bound to such soluble ligand analogue constructs from binding to immobilized ligand analogue on the terminal solid phase without utilizing a means to separate the soluble ligand analogue constructs from the reaction mixture. One skilled in the art will appreciate that the present invention contemplates this use of receptor conjugates and ligand analogue constructs for the detection of single or multiple target ligands.

Assay For Ligand Receptor Using Receptor Conjugate And Ligand Analogue Construct One skilled in the art will appreciate that ligand receptors can be the target analyte of interest. In this case receptor conjugate and a ligand analogue construct are provided in the reaction phase such that when sample suspected of containing target ligand receptor is added to form the reaction mixture, substantially all of the receptor conjugate is bound to ligand analogue construct and is prevented from binding to a terminal solid phase containing immobilized ligand if the reaction mixture contains ligand receptor at less than the threshold concentration of the assay. The amounts of receptor conjugate and ligand analogue construct are selected to provide a predetermined threshold ligand receptor concentration for the assay. One skilled in the art will appreciate that the present invention contemplates an assay for multiple ligand receptors by providing a complementary pair of receptor conjugate and ligand analogue construct and a discrete zone of immobilized ligand analogue on the terminal solid phase for each target ligand receptor.

While the present invention is particularly useful for the performance of competitive immunoassays, those skilled in the art will appreciate that the invention may be utilized for other ligand-receptor assays, including non-competitive immunoassays. In sandwich assays, for example, a ligand receptor can be provided together with a ligand receptor conjugate which binds to a different site on the ligand molecule in a reaction mixture. When sample suspected of containing ligand is added to the reaction phase, the binding of ligand receptor, ligand receptor conjugate, and ligand is allowed to achieve substantially equilibrium binding. The amount of ligand receptor is selected to bind a pre-determined amount of ligand such that when the reaction mixture is contacted with a solid phase containing immobilized ligand receptor, a known quantity of ligand receptor:-ligand:ligand receptor conjugate complex is prevented from binding to the solid phase and therefore no response is developed until the ligand concentration in the sample exceeds a selected threshold concentration.

Examples of ligands which would serve as suitable targets for the present invention include the following; ovulatory steroids and their metabolites: e.g., progesterone, estradiol, pregnanediol-3α-glucuronide, and estrone-3-glucuronide; drugs of abuse and their metabolites: e.g., amphetamine, barbiturates, benzodiazepines, cannabinoids, cocaine, methadone, methamphetamine, methaqualone, opiates, phencyclidine, propoxyphene, and tricyclic anti-depressants; therapeutic drugs and their metabolites: e.g., acetaminophen, digoxin, salicylate and theophylline; ovulatory hormones: e.g., human chorionic gonadotropin, and luteinizing hormone; thyroid hormones: e.g., triiodothyronine and thyroxine; mycotoxins: e.g., aflatoxin B1, aflatoxin B2, aflatoxin G1, aflatoxin M1, zearalenone, T-2 toxin, and deoxynivalenol; ciguatoxin; environmental toxins: e.g., polychlorinated biphenyls, dioxin, and ethylene dibromide; and proteins and antibodies of value in nosology: e.g., apolipoproteins, albumin, c-reactive protein and antibodies to hepatitis and HIV viruses. The following examples are offered by way of illustration and not by way of limitation.

Example 1

Preparation Of The N-Hydroxysuccinimide Ester Of Estrone-3-Glucuronide

Estrone-3-glucuronide (11.2 mg, 25 μmol) and N-hydroxysuccinimide (2.9 mg, 25 μmol) were dissolved in 0.1 mL dry dimethylformamide. Dicyclohexylcarbodiimide (5.7 mg, 27.5 μmol) was added and the flask was purged with nitrogen. The reaction was stirred at room temperature for 3 hours. The reaction mixture was filtered on a small fritted funnel to remove the precipitated dicyclohexylurea. The resulting N-hydroxysuccinimide ester was used immediately for conjugation to protein.

Preparation Of Estrone-3-Glucuronide Alkaline Phosphatase Conjugate

A solution of the N-hydroxysuccinimide ester of estrone-3-glucuronide (114 μl, 230 mM) in dimethylformamide was added to a solution of alkaline phosphatase (0.26 ml, 9.8 mg/ml) in 0.1 M potassium borate, 0.05 M potassium phosphate, 0.15 M sodium chloride, pH 8.75. The reaction mixture was stirred at room temperature for 12 hours. The estrone-3-glucuronide alkaline phosphatase conjugate was purified by chromatography on a Sephadex G-25 column.

Preparation Of Latex-Immobilized Affinity-Purified Goat IgG Antibody Against The Fc Fragment Of Mouse IgG Affinity-purified goat-anti-mouse Fc (Immunosearch) and polystyrene latex particles (sulfated, 1.07 μm) (Interfacial Dynamics) were incubated separately at 45° C. for one hour, the antibody solution being buffered with 0.1 M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in PBS containing 0.1% sodium azide at pH 7.0 at a latex concentration of 1% solids. This preparation was used to determine the immunoreactivities of conjugates and as an optional means for the removal of monoclonal antibody from the reaction mixture in the assay of estrone-3-glucuronide. A 1% suspension of this latex preparation was capable of binding 40 µg/ml of monoclonal antibody.

Measurement Of Conjugate Immunoreactivity

In order to determine the fraction of ligand analogue conjugate that could bind to antibody, monoclonal antibody specific for the target ligand was incubated with a quantity of ligand analogue conjugate such that sufficient antibody was available to bind to all conjugates that had bindable ligand attached. A quantity of goat-anti-mouse Fc latex was added in sufficient quantity to completely bind all of the monoclonal antibody together with any conjugate bound to it. The latex was separated from the mixture by centrifugation and the amount of enzyme activity remaining in the supernatant was assayed and compared to the total amount of enzyme activity added to the mixture. The percentage of immunoreactive conjugate was the percentage of total enzyme activity that was bound to the latex pellet. Conjugates which exhibited high immunoreactivities were representative of conjugates that were highly derivatized with ligand analogues while conjugates with low immunoreactivities were representative of conjugates that were less highly derivatized.

Assay For Estrone-3-Glucuronide Using An Optional Means For Removal Of Antibody From The Reaction Mixture A conjugate of estrone-3-glucuronide and alkaline phosphatase was prepared and its immunoreactivity was determined as described above using a monoclonal antibody, clone #27, obtained from Interpharm Laboratories, Rehovot, Israel. The conjugate was found to be 99.9% immunoreactive indicating that the enzyme was highly derivatized. Standards of estrone-3-glucuronide were prepared from dilutions of a 1 mM stock solution that was prepared by solubilization of a weighed quantity of estrone-3-glucuronide. Mixtures of the standards and the conjugate were prepared and 100 µl of each mixture was added to an equal volume of the monoclonal antibody at a concentration of 10 µg/ml in a suspension of 0.5% goat-anti-mouse Fc latex in microtiter plate wells. The mixtures, containing a final conjugate concentration of 4 nM and a final antibody concentration of 31 nM, were incubated for five minutes with gentle shaking before being subjected to centrifugation to pellet the latex. Fifty microliters of the supernatant from each well was added to microtiter plate wells containing immobilized monoclonal antibody, clone #27 (COBIND plates, Micro Membranes, antibody immobilized at 100 µg/ml using protocol specified by manufacturer) and incubated for 30 minutes at room temperature with gentle shaking. The wells were washed five times with borate buffered saline, pH 8.2, and the presence of bound enzyme activity was determined by adding 200 µl of 10mM phenolphthalein monophosphate, buffered by 2-amino-2-methyl-1-propanol at pH 10.2, and kinetically measuring the formation of phenolphthalein at 560 nm using a UV max microtiter plate reader (Molecular Devices). In addition, the enzyme activity remaining in the supernatant was determined by removing 10 µl of the supernatant after pelleting the latex, adding it to 200 µl of 10 mM phenolphthalein monophosphate, and kinetically measuring the rate of formation of phenolphthalein at 560 nm as described. The results are shown in Table I in relation to the concentration of estrone-3-glucuronide in the reaction mixture. The results clearly show that until the concentration of estrone-3-glucuronide reaches 30 nM, both the enzyme activity bound to anti-estrone-3-glucuronide in the wells and the enzyme activity in the supernatant remain at very low levels. The immunoreactive conjugate is substantially all bound to the antibody in the reaction mixture until the concentration of estrone-3-glucuronide exceeds the threshold concentration of the assay which in this case is approximately 30 nM. The enzyme activity bound to the immobilized antibody in the microtiter plate wells reaches a maximum before the free enzyme activity in the supernatant reaches a maximum because the amount of immobilized antibody in the wells is insufficient to bind all of the available conjugate in the presence of the concentrations of free estrone-3-glucuronide used here. The results indicate that a terminal solid phase with a higher potential capacity for the immobilization of antibodies would improve the dynamic range of response of this assay.

TABLE I

| [Estrone-3-Glucuronide] (nM) | Enzyme Activity Bound to Terminal Solid (mOD/min) | Enzyme Activity in Supernatant (mOD/min) |
|---|---|---|
| 0 | 0.3 | 0.8 |
| 10 | 0.4 | 0.6 |
| 20 | 0.4 | 0.4 |
| 30 | 5.3 | 2.6 |
| 40 | 4.1 | 3.1 |
| 50 | 2.7 | 3.5 |
| 60 | 4.8 | 5.5 |
| 70 | 6.8 | 6.7 |
| 80 | 12.6 | 9.4 |
| 90 | 10.2 | 9.2 |
| 100 | 10.2 | 10.6 |
| 200 | 18.8 | 23.3 |
| 500 | 16.8 | 37.1 |
| 1000 | 13.5 | 46.8 |

Assay For Estrone-3-Glucuronide Using A Membrane As A Terminal Solid Phase

Monoclonal antibody to estrone-3-glucuronide, clone 155B3 from Interpharm Laboratories, was immobilized on 16-well microtiter plates that contained Immobilon membrane as the bottom element of the wells (Millipore Corporation). The antibody was spotted onto each membrane-well by applying 0.6 µl of a solution containing 6 mg/ml antibody, 0.1 M potassium phosphate, 10 mg/ml tetrazole, and 0.1% polyvinyl alcohol (average molecular weight=2000), pH 7.4, and incubated for 20 minutes at room temperature before applying 20 µl of a solution containing 10 mg/ml casein, 0.1 M potassium phosphate, 10 mg/ml tetrazole, and 0.1% polyvinyl alcohol, pH 7.4, and incubating for 5 minutes. The excess solution was blotted with absorbent paper and the plates were dried in a desiccated container before use in assays as the terminal solid phase.

Assays were performed by mixing equal volumes of estrone-3-glucuronide standards and estrone-3-glucuronide-alkaline phosphatase conjugate and adding to these mixtures an amount of anti-estrone-3-glucuronide antibody selected so that the concentration range spanned by the standards included the expected threshold concentration determined by the selection of the antibody concentration. The total reaction volume was 60 μl for each mixture. After 10 minutes of incubation, 20 μl was removed from each reaction mixture and was added to the wells containing antibody immobilized on membranes. The membranes remained in contact with the reaction mixture for approximately one minute before each well was washed by vacuum-assisted filtration of three 200 μl volumes of borate-buffered saline containing 0.05% Lubrol PX at pH 8.2. The wells were rinsed by vacuum-assisted filtration of 50 μl of substrate solution containing 10 mM phenolphthalein monophosphate at pH 10.2. The wells were blotted by contacting the bottoms of the wells with absorbent paper and 50 μl of the same substrate solution was added to each well. The rate of formation of phenolphthalein was kinetically measured using a UV max microtiter plate reader (Molecular Devices) at 560 nm. When the instrument reading was complete, the wells were washed with 50 μl of a substrate solution containing 10 mM 5-bromo-4-chloro-3-indoxyl phosphate (BCIP) at pH 10.2, the wells were blotted with absorbent paper, and 50 μl of BCIP substrate was added to develop a visual assay response. After approximately 10 minutes, the reactions were stopped by adding 50 μl of 500 mM EDTA and blotting excess fluids from the membranes. The visual responses were compared to the instrumental measurements to confirm the development of specific signals; both visual and instrumental responses were in agreement for the assays described here and no visual response was detected for wells where the concentration of estrone-3-glucuronide was below the threshold concentration. The results of two such assays, one using a highly derivatized conjugate that exhibited an immunoreactivity of 90% and another using a sparsely derivatized conjugate exhibiting an immunoreactivity of 26%, are shown in Table II. The highly derivatized conjugate exhibited a threshold concentration of approximately 100 nM in this assay with a gradual increase in response up to a maximum reached at approximately 1000 nM. The assay utilizing the conjugate with 26% immunoreactivity exhibited a threshold concentration of approximately 120 nM and an assay response that increased more rapidly as a function of ligand concentration. We have found that the degree of derivatization as measured by the percentage immunoreactivity for the conjugate is a good predictor of the assay characteristics that will be exhibited by a particular conjugate. Highly derivatized conjugates result in assays that exhibit lower response slopes than less derivatized conjugates. This property can be used by one skilled in the art to optimize an assay for a specific application.

TABLE II

| [Estrone-3-Glucuronide] (nM) | 90% Immunoreactive Conjugate. Enzyme Activity Bound To Terminal Solid Phase (mOD/min) | 26% Immunoreactive Conjugate. Enzyme Activity Bound To Terminal Solid Phase (mOD/min) |
| --- | --- | --- |
| 0 | 0.0 | 0.0 |
| 20 | 0.0 | 0.0 |
| 40 | 0.1 | 0.0 |
| 60 | 0.0 | 0.0 |
| 80 | 0.0 | 0.1 |
| 100 | 0.2 | 0.1 |
| 120 | 0.3 | 0.4 |
| 140 | 0.3 | 1.0 |
| 160 | 0.9 | 2.9 |
| 180 | 1.2 | 4.0 |
| 200 | 1.6 | 4.3 |
| 1000 | 17.0 | 18.9 |

Determination of the Approach to Equilibrium in an Assay for Estrone-3-Glucuronide In order to determine the incubation time needed for the reaction mixture to approach substantially equilibrium binding conditions, the most important parameter to examine is the assay response in the immediate vicinity of the threshold concentration because the approach to equilibrium is slowest at these concentrations of target ligand. A useful method is to perform the assay using target ligand concentrations above and below the threshold concentration and to examine the effect of variation in the incubation time of the reaction mixture on the assay response at these concentrations. The assay for estrone-3-glucuronide was performed as described in the previous example using a membrane as the terminal solid phase and the conjugate exhibiting 26% immunoreactivity, and using estrone-3-glucuronide standards such that the concentration in the reaction mixture was either 100 or 140 nM, bracketing the observed threshold concentration of 120 nM. The reaction mixtures were incubated for 1, 3, 6 or 10 minutes to determine the minimum time necessary to approach substantially equilibrium binding conditions. The results shown in Table III indicate that an incubation time of six minutes is sufficient so that no visually detectable signal is observed in assays containing 100 nM estrone-3-glucuronide while the assay response of assays containing 140 nM remains visually detectable.

TABLE III

| Reaction Mixture (mOD/min) Incubation Time (min) | Enzyme Activity Bound to Terminal Solid Phase | |
| --- | --- | --- |
| | 100 nM | 140 nM |
| 1 | 0.6 | 2.5 |
| 3 | 0.3 | 1.4 |
| 6 | 0.05 | 1.1 |
| 10 | 0.0 | 3.5 |

EXAMPLE 2

Preparation Of The N-Hydroxysuccinimide Ester Of 5β-Pregnane-3α,20α-Diol Glucuronide Pregnanediol glucuronide (13.3 mg, 25 μmol) and N-hydroxysuccinimide (2.9 mg, 25 μmol) were dissolved in 0.1 mL dry dimethylformamide. Dicyclohexylcarbodiimide (5.7 mg, 27.5 μmol) was added and the flask was purged with nitrogen. The reaction was stirred at room temperature for 3 hours. The reaction mixture was filtered on a small fritted funnel to remove the precipitated dicyclohexylurea and the solvent was removed in vacuo. Anhydrous methanol was added to the residue and the flask was placed at −20° C. to precipitate the N-hydroxysuccinimide ester. The resulting crystals (12 mg) were isolated, dried, and stored desiccated at −20° C.

Preparation Of Pregnanediol-3α-Glucuronide-Alkaline Phosphatase Conjugate

The N-hydroxysuccinimide ester of pregnanediol glucuronide was dissolved in dry acetonitrile and reacted with alkaline phosphatase at 8 mg/ml protein using a tenfold molar excess of the N-hydroxysuccinimide ester. The reaction was performed in phosphate-buffered-saline at a pH of 7.0 for 90 minutes. The protein was removed from reactants by G-25 chromatography and its immunoreactivity was measured as described above and found to be 96%.

Assay For Pregnanediol-3α-Glucuronide Using A Membrane As A Terminal Solid Phase A monoclonal antibody for pregnanediol-3α-glucuronide (clone P44, Interpharm Laboratories) was immobilized on Immobilon membranes in 16-well microtiter plates as described above except that the antibody concentration used for immobilization was 16 mg/ml. Assays were performed by mixing equal volumes of pregnanediol-3α-glucuronide standards and pregnanediol-3α-glucuronide-alkaline phosphatase conjugate and adding to these mixtures an amount of anti-pregnanediol-3α-glucuronide antibody selected so that the concentration range spanned by the standards included the threshold concentration determined by the selection of the antibody concentration. The total reaction mixture volume was 60 μl for each mixture. The reaction mixture was incubated for 10 minutes and all remaining assay procedures were performed as described above in the assays for estrone-3-glucuronide. The results are shown in Table IV and reflect a threshold concentration of approximately 3 μM for the first visually detectable result. The results further exhibit a "hook" effect that can be observed in such immunoassays where the combination of free ligand and free ligand analogue conjugate in the reaction mixture is in substantial excess over the amount of immobilized receptor on the terminal solid phase. When the maximum assay response, developed in this assay at approximately 50 μM, is compared to the maximum potential response that could be achieved if all of the free ligand analogue conjugate were bound to the terminal solid phase (determined by contacting reaction mixture containing conjugate only with the terminal solid phase), only 4% of the potentially available response is achieved in this assay. The use of terminal solid phases with increased amounts of immobilized antibody, the use of highly derivatized conjugates that can compete effectively with ligand for binding sites on the terminal solid phase, and the use of high concentrations of ligand analogue conjugate are all effective ways of improving the maximum response in assays where the threshold concentration is high so that the danger of a substantial "hook" effect is minimized. The combination of these parameters that is used to optimize an assay is understood by those skilled in the art to be dependent on the objectives of a particular immunoassay application.

TABLE IV

| [Pregnanediol-3α-Glucuronide] (μM) | Enzyme Activity Bound To Terminal Solid Phase (mOD/min) |
| --- | --- |
| 0 | 0.0 |
| 1 | 0.1 |
| 2 | 0.3 |
| 3 | 0.9 |
| 4 | 1.6 |

TABLE IV-continued

| [Pregnanediol-3α-Glucuronide] (μM) | Enzyme Activity Bound To Terminal Solid Phase (mOD/min) |
| --- | --- |
| 5 | 2.7 |
| 6 | 2.9 |
| 7 | 2.7 |
| 8 | 3.9 |
| 9 | 4.7 |
| 10 | 4.1 |
| 20 | 4.8 |
| 50 | 6.5 |
| 100 | 4.5 |

EXAMPLE 3

Simultaneous Multiple Assay for Drugs of Abuse

The following example illustrates the application of the invention to an assay for a drugs of abuse panel. A drugs of abuse panel useful for screening urine samples would include the five drugs considered of greatest importance by the National Institute of Drug Abuse, (NIDA), amphetamine, cocaine, opiates, phencyclidine, and cannibinoids. Development of antibodies for these haptens requires the synthesis of immunogens. Methods for the synthesis of such immunogens are known to those skilled in the art, see for example, U.S. Pat. Nos. 3,817,837, 3,878,187, 3,884,898, 4,203,802 and 4,281,065, and Rodgers, R., Crowl, C. P., Eimstad, W. M., Hu, M. W., Kam, J. K., Ronald, R. C., Rowley, G. L., and Ullman, E. F., Clin. Chem., 24, 95-100 (1978). The immunogens produced by said methods are then used to immunize mice for the purposes of eliciting an immune response to the desired drugs. Subsequent to the elicitation of an immune response, the mice are sacrificed and the spleen cells are fused with myeloma cells to produce antibody secreting hybridoma cell lines. Further characterization of the antibodies derived from the cell lines is achieved by utilizing the immunogens used in the immunization protocols. The methods for producing and characterizing monoclonal antibodies are well known to those skilled in the art, see for example, Liu, D., Purssell, R., and Levy, J. G., Clinical Toxicology, 25, 527-538 (1987). The drugs and chemistry used in the creation of immunogens are also used in the synthesis of drug-enzyme conjugates which consist of enzymes such as calf intestine alkaline phosphatase derivatized with target drugs. Methods for the preparation of such drug derivatized enzymes are known to those skilled in the art, see for example, U.S Pat. Nos. 3,817,837 and 4,203,802.

A reaction phase is constructed from appropriate amounts of the drug-enzyme conjugates and the monoclonal antibodies directed against the NIDA drug panel. The amounts of the antibodies are selected such that the assay determined threshold drug concentrations are consistent with the NIDA recommendations for the screening of positive from negative samples. Those threshold concentrations are amphetamine, 1000 ng/ml, cannabinoids, 100 ng/ml, cocaine, 300 ng/ml, opiates, 300 ng/ml, and phencyclidine, 25 ng/ml. The sample is mixed with the reaction phase to form a reaction mixture, which is allowed to react until the multiple competition reactions have substantially approached equilibrium binding conditions. The reaction mixture is then placed in contact with a test device which comprises in part a membrane upon which has been immobilized anti-drug antibodies in separate discrete reaction zones. The number of anti-drug reaction zones matches the number of drug-enzyme conjugate::anti-drug antibody pairs. Methods for the immobilization of antibodies upon membranes are well known to those skilled in the art, see for example Pluskal, M. G., Przekop, M. B., Kavonian, M. R., Vecoli, D., Hicks, D. A., BioTechniques, 4, 272–283 (1986). Drug-enzyme conjugate which was unbound to soluble anti-drug antibody at the completion of the reaction in the reaction mixture, then complexes with anti-drug antibody immobilized in the drug specific reaction zone on the membrane. A wash solution is used to separate any remaining free drugenzyme conjugate in the reaction mixture from the membrane bound drug-enzyme conjugate. The membrane is then contacted with a solution containing an appropriate enzyme substrate capable of developing a visible color, e.g. for calf intestine alkaline phosphatase a solution containing 3-indoxyl phosphate would be suitable. Color development is allowed to occur and the response of each reaction zone is interpreted such that the absence of detectable color indicates that the drug targeted by that zone is at a concentration less than the threshold concentration, while the presence of detectable color indicates that the target drug is present at a concentration substantially equivalent to or greater than the threshold concentration. Each reaction zone is individually interpreted thus allowing all five target drugs to be assessed as positive or negative relative to the NIDA specified threshold concentrations.

We claim:

1. Method for determining the presence of at least one target ligand, capable of competing with a ligand analogue conjugate for binding sites available on a ligand receptor, said ligand analogue conjugate comprising at least one ligand analogue coupled to a signal development element capable of emitting a detectable signal, in a fluid sample suspected of containing said target ligand, comprising the steps of:
   a. contacting said fluid sample with said ligand analogue conjugate and said ligand receptor to form a homogeneous reaction mixture, the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugant is detected as a result of the assay method;
   b. detecting unbound ligand analogue conjugate in said reaction mixture;
   c. relating the detectable signal to the presence of said target ligand in said fluid sample.

2. Method for determining the presence of at least one target ligand, capable of competing with a ligand analogue conjugate for binding sites available on a ligand receptor, said ligand analogue conjugate comprising at least one ligand analogue coupled to a signal development element capable of emitting a detectable signal, in a fluid sample suspected of containing said target ligand, comprising the steps of:
   a. contacting said fluid sample with said ligand analogue conjugate and said ligand receptor to form a homogeneous reaction mixture, the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugate is detected as a result of the assay method;
   b. removing ligand receptor from said reaction mixture;
   c. detecting unbound ligand analogue conjugate in said reaction mixture;
   d. relating the detectable signal to the presence of said target ligand in said fluid sample.

3. Method for determining the presence of at least one target ligand at or above at least one predetermined threshold ligand concentration, said target ligand capable of competing with a ligand analogue conjugate for binding sites available on a ligand receptor, said ligand analogue conjugate comprising at least one ligand analogue coupled to a signal development element capable of emitting a detectable signal, in a fluid sample suspected of containing said target ligand, comprising the steps of:
   a. contacting said fluid sample with said ligand analogue conjugate and said ligand receptor to form a homogeneous reaction mixture;
      (i) the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugate is detected as a result of the assay method; and
      (ii) the relative and absolute amounts of ligand analogue conjugate and ligand receptor being selected such that at least one of said predetermined threshold ligand concentration(s) is established below which no unbound ligand analogue conjugate is detected as a result of the assay method;
   b. detecting unbound ligand analogue conjugate in said reaction mixture;
   c. relating the detectable signal to the presence of said target ligand at or above said predetermined threshold ligand concentration in said fluid sample.

4. Method for determining the presence of at least one target ligand at or above at least one predetermined threshold ligand concentration, said target ligand capable of competing with a ligand analogue conjugate for binding sites available on a ligand receptor, said ligand analogue conjugate comprising at least ligand analogue coupled to a signal development element capable of emitting a detectable signal, in a fluid sample suspected of containing said target ligand, comprising the steps of:
   a. contacting said fluid sample with said ligand analogue conjugate and said ligand receptor to form a homogeneous reaction mixture;
      (i) the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugate is detected as a result of the assay method; and
      (ii) the relative and absolute amounts of ligand analogue conjugate and ligand receptor being selected such that at least one of said predetermined threshold ligand concentration is established below which no unbound ligand analogue conjugate is detected as a result of the assay method;

b. removing ligand receptor from said reaction mixture;

c. detecting unbound ligand analogue conjugate in said reaction mixture;

d. relating the detectable signal to the presence of said target ligand at or above said predetermined threshold ligand concentration in said fluid sample.

5. Method of claim 2 or 4 wherein a solid support means is used in step (b) to remove ligand receptor from said reaction mixture.

6. Method of claim 5 wherein at least one receptor is immobilized on said solid support.

7. Method of claim 5 wherein said solid support means is selected from the group consisting of diffusible beads and porous matrices.

8. Method of claim 2 or 4 wherein in step (b) ligand receptor is removed from said reaction mixture by precipitation.

9. Method of claim 8 wherein at least one receptor is used to precipitate ligand receptor.

10. Method of claim 2 or 4 wherein at least one of said ligand receptors in said reaction mixture is a ligand complement-ligand receptor molecule and said reaction mixture is contacted with at least one ligand complement receptor capable of binding thereto, and wherein said ligand complement receptor is used to remove said ligand complement-ligand receptor molecule from said reaction mixture.

11. Method of claim 10 wherein said ligand complement receptor is avidin and said ligand complement-ligand receptor molecule is biotin covalently bound to said ligand receptor.

12. Method of claim 1 or 2 or 3 or 4 wherein said ligand receptor undergoes diffusive motion during the competition for ligand receptor binding sites which occurs between ligand and ligand analogue conjugate.

13. Method of claim 1 or 2 or 3 or 4 wherein said ligand receptor is immobilized on a non-diffusive solid phase.

14. Method of claim 1 or 2 or 3 or 4 wherein said method is an immunoassay in which the ligand receptor is an antibody.

15. Method of claim 14 wherein said antibody is monoclonal.

16. Method of claim 1 or 2 or 3 or 4 wherein the number of ligand analogues coupled to said signal development element is between 1 and 50.

17. Method of claim 1 or 2 or 3 or 4 wherein the number of ligand analogues coupled to said signal development element is between 1 and 10.

18. Method of claim 1 or 2 or 3 or 4 further comprising at least one ligand receptor immobilized on a solid phase in at least one distinct locus for the detection of at least one unbound ligand analogue conjugate in said reaction mixture.

19. Method of claim 18 wherein said solid phase is selected from the group consisting of porous and non-porous matrices.

20. Method of claim 2 or 4 wherein said reaction mixture contains at least one ligand complement-ligand analogue conjugate and wherein at least one ligand complement receptor is immobilized on a solid phase in at least one distinct locus for the detection of at least one unbound ligand complement-ligand analogue conjugate in said reaction mixture.

21. Method of claim 2 or 4 wherein said reaction mixture contains at least one ligand complement-ligand analogue conjugate and wherein at least one ligand receptor and at least one ligand complement receptor are immobilized on a solid phase in at least one distinct locus for the detection of at least one unbound ligand analogue conjugate and at least one unbound ligand complement-ligand analogue conjugate in said reaction mixture.

22. Method of claim 3 or 4 further comprising at least one ligand receptor immobilized on a solid phase in at least one distinct locus for the detection of at least one unbound ligand analogue conjugate in said reaction mixture, wherein a detectable signal at each locus signifies the presence of ligand at or above a predetermined threshold ligand concentration specific for that locus.

23. Method of claim 1 or 2 or 3 or 4 wherein said signal development element is detected by non-instrumental means.

24. Method of claim 23 wherein said signal development element is detected by visual means.

25. Method of claim 1 or 2 or 3 or 4 wherein the signal development element is an enzyme.

26. Method for determining the presence of at least one target ligand receptor, capable of competing with a ligand receptor conjugate for binding sites available on a ligand analogue construct, said ligand receptor conjugate comprising at least one ligand receptor coupled to a signal development element capable of emitting a detectable signal, in a fluid sample suspected of containing said target ligand receptor, comprising the steps of:

a. contacting said fluid sample with said ligand receptor conjugate and said ligand analogue construct to form a homogeneous reaction mixture, the relative amounts of said ligand receptor conjugate and said ligand analogue construct being selected such that in the absence of said target ligand receptor, and subsequent to substantially equilibrium binding in said reaction mixture, substantially all of said ligand receptor conjugate is bound to said ligand analogue construct such that no unbound ligand receptor conjugate is detected as a result of the assay method;

b. detecting unbound ligand receptor conjugate in said reaction mixture;

c. relating the detectable signal to the presence of said target ligand receptor in said fluid sample.

27. Method for determining the presence of at least one target ligand receptor, capable of competing with a ligand receptor conjugate for binding sites available on a ligand analogue construct, said ligand receptor conjugate comprising at least one ligand receptor coupled to a signal development element capable of emitting a detectable signal, in a fluid sample suspected of containing said target ligand receptor, comprising the steps of:

a. contacting said fluid sample with said ligand receptor conjugate and said ligand analogue construct to form a homogeneous reaction mixture, the relative amounts of said ligand receptor conjugate and said ligand analogue construct being selected such that in the absence of said target ligand receptor, and subsequent to substantially equilibrium binding in said reaction mixture, substantially all of said ligand receptor conjugate is bound to said ligand analogue construct such that no unbound ligand receptor conjugate is detected as a result of the assay method;
b. removing ligand analogue construct from said reaction mixture;
c. detecting unbound ligand receptor conjugate in said reaction mixture;
d. relating the detectable signal to the presence of said target ligand receptor in said fluid sample.

28. Method for determining the presence of at least one target ligand receptor at or above at least one predetermined threshold ligand receptor concentration, said target ligand receptor capable of competing with a ligand receptor conjugate for binding sites available on said ligand analogue construct, said ligand receptor conjugate comprising at least one ligand receptor coupled to a signal development element capable of emitting a detectable signal, in a fluid sample suspected of containing said target ligand receptor, comprising the steps of:
   a. contacting said fluid sample with said ligand receptor conjugate and said ligand analogue construct to form a homogeneous reaction mixture;
      (i) the relative amounts of said ligand receptor conjugate and said ligand analogue construct being selected such that in the absence of said target ligand receptor, and subsequent to substantially equilibrium binding in said reaction mixture, substantially all of said ligand receptor conjugate is bound to said ligand analogue construct such that no unbound ligand receptor conjugate is detected as a result of the assay method; and
      (ii) the relative and absolute amounts of ligand receptor conjugate and ligand analogue construct being selected such that at least one of said predetermined threshold ligand receptor concentration(s) is established below which no unbound ligand receptor conjugate is detected as a result of the assay method;
   b. detecting unbound ligand receptor conjugate in said reaction mixture;
   c. relating the detectable signal to the presence of said target ligand receptor at or above said predetermined threshold ligand receptor concentration(s) in said fluid sample.

29. Method for determining the presence of at least one target ligand receptor at or above at least one predetermined threshold ligand receptor concentration, said target ligand receptor capable of competing with a ligand receptor conjugate for binding sites available on a ligand analogue construct, said ligand receptor conjugate comprising at least one ligand receptor coupled to a signal development element capable of emitting a detectable signal, in a fluid sample suspected of containing said target ligand receptor, comprising the steps of:
   a. contacting said fluid sample with said ligand receptor conjugate and said ligand analogue construct to form a homogeneous reaction mixture;
      (i) the relative amounts of said ligand receptor conjugate and said ligand analogue construct being selected such that in the absence of said target ligand receptor, and subsequent to substantially equilibrium binding in said reaction mixture, substantially all of said ligand receptor conjugate is bound to said ligand analogue construct such that no unbound ligand receptor conjugate is detected as a result of the assay method; and
      (ii) the relative and absolute amounts of said ligand receptor conjugate and ligand analogue construct being selected such that at least one of said predetermined threshold ligand receptor concentration(s) is established below which no unbound ligand receptor conjugate is detected as a result of the assay method;
   b. removing ligand analogue construct from said reaction mixture;
   c. detecting unbound ligand receptor conjugate in said reaction mixture;
   d. relating the detectable signal to the presence of said target ligand receptor at or above said predetermined threshold ligand receptor concentration(s) in said fluid sample.

30. Method of claim 27 or 29 wherein a solid support means is used in step (b) to remove ligand analogue construct from said reaction mixture.

31. Method of claim 30 wherein at least one receptor is immobilized on said solid support.

32. Method of claim 30 wherein said solid support means is selected from the group consisting of diffusible beads and porous matrices.

33. Method of claim 27 or 29 wherein in step (b) ligand analogue construct is removed from said reaction mixture by precipitation.

34. Method of claim 33 wherein at least one (ligand analogue construct) receptor is used to precipitate ligand analogue construct.

35. Method of claim 27 or 29 wherein at least one of said ligand analogue constructs in said reaction mixture is a ligand complement-ligand analogue construct and said reaction mixture is contacted with at least one ligand complement receptor capable of binding thereto, and wherein said ligand complement receptor is used to remove said ligand complement-ligand analogue construct from said reaction mixture.

36. Method of claim 35 wherein said ligand complement-ligand analogue construct is biotin covalently bound to said ligand analogue construct and said ligand complement receptor is avidin.

37. Method of claim 26 or 27 or 28 or 29 wherein said ligand analogue construct undergoes diffusive motion during the competition for ligand analogue binding sites which occurs between said target ligand receptor and said ligand receptor conjugate.

38. Method of claim 26 or 27 or 28 or 29 wherein said ligand analogue construct is immobilized on a non-diffusive solid phase.

39. Method of claim 26 or 27 or 28 or 29 wherein said method is an immunoassay in which the ligand receptor is an antibody.

40. Method of claim 26 or 27 or 28 or 29 further comprising at least one ligand analogue immobilized on a solid phase in at least one distinct locus for the detection of at least one unbound ligand receptor conjugate in said reaction mixture.

41. Method of claim 40 wherein said solid phase is selected from the group consisting of porous and nonporous matrices.

42. Method of claim 27 or 29 wherein said reaction mixture contains at least one ligand complement-ligand receptor conjugate molecule and wherein at least one ligand complement receptor is immobilized on a solid phase in at least one distinct locus for the detection of at least one unbound ligand complement-ligand receptor conjugate molecule in said reaction mixture.

43. Method of claim 27 or 29 wherein the reaction mixture also contains at least one ligand complement-ligand receptor conjugate molecule and wherein at least one ligand analogue and at least one ligand complement receptor are immobilized on a solid phase in at least one distinct locus for the detection of at least one unbound ligand receptor conjugate and at least one unbound ligand complement-ligand receptor conjugate molecule in said reaction mixture.

44. Method of claim 28 or 29 further comprising at least one ligand analogue immobilized son a solid phase in at least one distinct locus for the detection of at least one unbound ligand receptor conjugate in said reaction mixture, wherein a detectable signal at each locus signifies the presence of ligand receptor at or above a predetermined threshold ligand receptor concentration specific for that locus.

45. Method of claim 26 or 27 or 28 or 29 wherein said signal development element is detected by non-instrumental means.

46. Method of claim 45 wherein said signal development element is detected by visual means.

47. Method of claim 26 or 27 or 28 or 29 wherein the signal development element is an enzyme.

48. Method for determining the presence of at least one target ligand, capable of competing with a ligand analogue construct for binding sites available on a ligand receptor conjugate, said ligand receptor conjugate comprising at least one ligand receptor coupled to a signal development element capable of emitting a detectable signal, in a fluid sample suspected of containing said target ligand, comprising the steps of:
 a. contacting said fluid sample with said ligand receptor conjugate and said ligand analogue construct to form a homogeneous reaction mixture, the relative amounts of said ligand receptor conjugate and said ligand analogue construct being selected such that in the absence of said target ligand, and subsequent to substantially equilibrium binding in said reaction mixture, substantially all of said ligand receptor conjugate is bound to said ligand analogue construct such that no unbound ligand receptor conjugate is detected as a result of the assay method;
 b. detecting unbound ligand receptor conjugate in said reaction mixture;
 c. relating the detectable signal to the presence of said target ligand in said fluid sample.

49. Method for determining the presence of at least one target ligand, capable of competing with a ligand analogue construct for binding sites available on a ligand receptor conjugate, said ligand receptor conjugate comprising at least one ligand receptor coupled to a signal development element capable of emitting a detectable signal, in a fluid sample suspected of containing said target ligand, comprising the steps of:
 a. contacting said fluid sample with said ligand receptor conjugate and said ligand analogue construct to form a homogenous reaction mixture, the relative amounts of said ligand receptor conjugate and said ligand analogue construct being selected such that in the absence of said target ligand, and subsequent to substantially equilibrium binding in said reaction mixture, substantially all of said ligand receptor conjugate is bound to said ligand analogue construct such that no unbound ligand receptor conjugate is detected as a result of the assay method;
 b. removing ligand analogue construct from said reaction mixture;
 c. detecting unbound ligand receptor conjugate in said reaction mixture;
 d. relating the detectable signal to the presence of said target ligand in said fluid sample.

50. Method for determining the presence of at least one target ligand at or above at least one predetermined threshold ligand concentration, said target ligand capable of competing with a ligand analogue construct for binding sites available on a ligand receptor conjugate, said ligand receptor conjugate comprising at least one ligand receptor coupled to a signal development element capable of emitting a detectable signal, in a fluid sample suspected of containing said target ligand, comprising the steps of:
 a. contacting said fluid sample with said ligand receptor conjugate and said ligand analogue construct to form a homogeneous reaction mixture;
  (i) the relative amounts of said ligand receptor conjugate and said ligand analogue construct being selected such that in the absence of said target ligand, and subsequent to substantially equilibrium binding in said reaction mixture, substantially all of said ligand receptor conjugate is bound to said ligand analogue construct such that no unbound ligand receptor conjugate is detected as a result of the assay method; and
  (ii) the relative and absolute amounts of ligand receptor conjugate and ligand analogue construct being selected such that at least one of said predetermined threshold ligand concentration(s) is established below which no unbound ligand receptor conjugate is detected as a result of the assay method;
 b. detecting unbound ligand receptor conjugate in said reaction mixture;
 c. relating the detectable signal to the presence of said target ligand at or above said predetermined threshold ligand concentration(s) in said fluid sample.

51. Method for determining the presence of at least one target ligand at or above at least one predetermined threshold ligand concentration, said target ligand capable of competing with a ligand analogue construct for binding sites available on a ligand receptor conjugate, said ligand receptor conjugate comprising at least one ligand receptor coupled to a signal development element capable of emitting a detectable signal, in a fluid sample suspected of containing said target ligand, comprising the steps of:
 a. contacting said fluid sample with said ligand receptor conjugate and said ligand analogue construct to form a homogenous reaction mixture;
  (i) the relative amounts of said ligand receptor conjugate and said ligand analogue construct being selected such that in the absence of said target ligand, and subsequent to substantially equilibrium binding in said reaction mixture, substantially all of said ligand receptor conjugate is bound to said ligand analogue construct such that no unbound ligand receptor conjugate is detected as a result of the assay method; and
  (ii) the relative and absolute amounts of ligand receptor conjugate and ligand analogue construct being selected such that at least one of said predetermined threshold ligand concentration(s) is established below which no unbound ligand receptor conjugate is detected as a result of the assay method;

b. removing ligand analogue construct from said reaction mixture;
c. detecting unbound ligand receptor conjugate in said reaction mixture;
d. relating the detectable signal to the presence of said target ligand at or above said predetermined threshold ligand concentration(s) in said fluid sample.

52. Method of claim 49 or 51 wherein a solid support means is used in step (b) to remove ligand analogue construct from said reaction mixture.

53. Method of claim 52 wherein said solid support means is selected from the group consisting of diffusible beads and porous matrices.

54. Method of claim 49 or 51 wherein in step (b) ligand analogue construct is removed from said reaction mixture by precipitation.

55. Method of claim 49 or 51 wherein at least one of said ligand analogue constructs in said reaction mixture is a ligand complement-ligand analogue construct and said reaction mixture is contacted with at least one ligand complement receptor capable of binding thereto, and wherein said ligand complement receptor is used to remove said ligand complement-ligand analogue construct from said reaction mixture.

56. Method of claim 55 wherein said ligand complement-ligand analogue construct is biotin covalently bound to said ligand analogue construct and said ligand complement receptor is avidin.

57. Method of claim 52 or 53 or 54 or 55 wherein said ligand analogue construct undergoes diffusive motion during the competition for ligand receptor conjugate binding sites which occurs between ligand and ligand analogue construct.

58. Method of claim 48 or 49 or 50 or 51 wherein the ligand analogue construct is immobilized on a non-diffusive solid phase.

59. Method of claim 48 or 49 or 50 or 51 wherein said method is an immunoassay in which the ligand receptor is an antibody.

60. Method of claim 59 wherein said antibody is monoclonal.

61. Method of claim 48 or 49 or 50 or 51 further comprising at least one ligand analogue immobilized on a solid phase in at least one distinct locus for the detection of at least one unbound ligand receptor conjugate in said reaction mixture.

62. Method of claim 61 wherein said solid phase is selected from the group consisting of porous and non-porous matrices.

63. Method of claim 49 or 51 wherein the reaction mixture contains at least one ligand complement-ligand receptor conjugate molecule and wherein at least one ligand complement receptor is immobilized on a solid phase in at least one distinct locus for the detection of at least one unbound ligand complement-ligand receptor conjugate molecule in said reaction mixture.

64. Method of claim 49 or 51 wherein the reaction mixture also contains at least one ligand complement-ligand receptor conjugate molecule and wherein at least one ligand analogue and at least one ligand complement receptor are immobilized on a solid phase in at least one distinct locus for the detection of at least one unbound ligand receptor conjugate and at least one unbound ligand complement-ligand receptor conjugate molecule in said reaction mixture.

65. Method of claim 50 or 51 further comprising at least one ligand analogue immobilized on a solid phase in at least one distinct locus for the detection of at least one unbound ligand receptor conjugate in said reaction mixture wherein a detectable signal at each locus signifies the presence of ligand at or above a predetermined threshold ligand concentration specific for that locus.

66. Method of claim 48 or 49 or 50 or 51 wherein said signal development element is detected by non-instrumental means.

67. Method of claim 66 wherein said signal development element is detected by visual means.

68. Method of claim 48 or 49 or 50 or 51 wherein the signal development element is an enzyme.

69. Method of claims 1 or 2 or 3 or 4 or 26 or 27 or 28 or 29 or 48 or 49 or 50 or 51 wherein said reaction mixture also contains a negative control ligand conjugate and a negative control ligand receptor such that subsequent to substantially equilibrium binding in said reaction mixture, substantially all of the negative control ligand conjugate is bound to negative control ligand receptor such that no unbound negative control ligand conjugate is detected as a result of the assay method and wherein the detection of unbound negative control ligand conjugate in the reaction mixture as a result of the assay method is an indication of an invalid method result.

70. Method of claims 3 or 4 or 28 or 29 or 50 or 51 wherein detection is by visual means and wherein said reaction mixture contains at least one reference ligand conjugate wherein the detection of reference ligand conjugate defines at least one reference concentration for at least one target ligand which is used in conjunction with said predetermined threshold concentration to relate said assay response to a range of target concentration(s).

* * * * *